United States Patent
Cariola et al.

(10) Patent No.: US 12,171,936 B2
(45) Date of Patent: Dec. 24, 2024

(54) IMPELLER FOR A RESPIRATORY DEVICE

(71) Applicant: ResMed Pty Ltd, Bella Vista (AU)

(72) Inventors: Melanie Lucia Cariola, Sydney (AU); Barton John Kenyon, Sydney (AU); Ryan Spindler, Porter Ranch, CA (US); Hargopal Verma, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 18/141,502

(22) Filed: May 1, 2023

(65) Prior Publication Data

US 2023/0263977 A1    Aug. 24, 2023

Related U.S. Application Data

(63) Continuation of application No. 16/485,591, filed as application No. PCT/AU2018/050109 on Feb. 13, 2018, now Pat. No. 11,672,932.

(Continued)

(51) Int. Cl.
*A61M 16/00*    (2006.01)
*F04D 29/28*    (2006.01)
(Continued)

(52) U.S. Cl.
CPC ....... *A61M 16/0066* (2013.01); *F04D 29/281* (2013.01); *F04D 29/30* (2013.01);
(Continued)

(58) Field of Classification Search
CPC .. F04D 29/281; F04D 29/30; A61M 16/00066
See application file for complete search history.

(56) References Cited

U.S. PATENT DOCUMENTS 2,469,458 A    5/1949    Dunnells et al.
4,008,985 A *  2/1977    Schemmann ........... F04D 13/06
                                                        415/141

(Continued)

FOREIGN PATENT DOCUMENTS

CN    101449064 A    6/2009
CN    101589235 A    11/2009

(Continued)

OTHER PUBLICATIONS

KR-200447433-translation from Espacenet (Year: 2004).*

(Continued)

*Primary Examiner* — Brian P Wolcott
*Assistant Examiner* — Behnoush Haghighian
(74) *Attorney, Agent, or Firm* — Nixon & Vanderhye P.C.

(57) ABSTRACT

A compact respiratory therapy device suitable for use by a patient during sleep to provide respiratory pressure therapy such as at a pressure between 4-30 cmH2O includes a housing, an inlet, an outlet, a motor including a rotor, and an impeller configured to be rotated by the rotor to deliver a flow of air from the inlet toward the outlet. The impeller includes a set of impeller blades, each impeller blade comprising a leading edge and a trailing edge; and a first shroud and a second shroud, each shroud at least partly defining a flow passage through the impeller, the first shroud comprising a wall defining a periphery of an impeller inlet. The compact respiratory therapy device is configured to deliver the flow of air from the outlet for delivery to the patient at a pressure between 4-30 cmH2O at an overall sound power level of less than 50 dB(A) thereby reducing any disturbance to a quality of sleep for the patient. A diameter of the impeller is less than 50 mm. The first shroud and the second shroud are configured such that the flow passage is narrower in an axial direction at an outer portion of the impeller than (Continued)

at an inner portion of the impeller; and a diameter of the impeller inlet is at least 50% of the diameter of the impeller.

8 Claims, 33 Drawing Sheets

Related U.S. Application Data

(60) Provisional application No. 62/512,445, filed on May 30, 2017, provisional application No. 62/458,862, filed on Feb. 14, 2017.

(51) Int. Cl.
  *F04D 29/30* (2006.01)
  *F04D 29/66* (2006.01)
  *F04D 25/08* (2006.01)

(52) U.S. Cl.
  CPC ....... *F04D 29/666* (2013.01); *A61M 2205/42* (2013.01); *A61M 2207/00* (2013.01); *F04D 25/08* (2013.01); *F04D 29/668* (2013.01)

(56) References Cited

U.S. PATENT DOCUMENTS

| | | | |
|---|---|---|---|
| 4,782,832 A | 11/1988 | Trimble et al. | |
| 4,944,310 A | 7/1990 | Sullivan | |
| 6,532,959 B1 | 3/2003 | Berthon-Jones | |
| 6,581,594 B1 | 6/2003 | Drew et al. | |
| 7,108,482 B2* | 9/2006 | Chapman | F04D 29/162 415/206 |
| 7,866,944 B2* | 1/2011 | Kenyon | F04D 25/08 415/206 |
| 8,096,783 B2* | 1/2012 | Grasmuck | F04D 25/082 415/58.4 |
| 8,272,837 B2* | 9/2012 | Kenyon | F04D 29/30 415/199.2 |
| 8,393,320 B2 | 3/2013 | Kenyon | |
| 8,403,639 B2* | 3/2013 | Vedsted | F04D 29/4286 415/208.2 |
| 8,636,479 B2* | 1/2014 | Kenyon | F04D 25/0646 417/423.5 |
| 8,638,014 B2 | 1/2014 | Sears et al. | |
| 8,733,349 B2 | 5/2014 | Bath et al. | |
| 9,004,067 B2* | 4/2015 | Kenyon | A61M 16/0057 415/206 |
| 9,039,360 B2* | 5/2015 | Fukuda | F04D 29/4226 415/204 |
| 9,132,252 B2 | 9/2015 | Barlow | |
| 9,512,856 B2* | 12/2016 | Nibu | F04D 29/4246 |
| 9,850,764 B2* | 12/2017 | Care | B23P 15/04 |
| 10,578,118 B2* | 3/2020 | Nibu | A61M 16/0069 |
| 10,975,880 B2* | 4/2021 | Nibu | A61M 16/0875 |
| 2005/0163614 A1* | 7/2005 | Chapman | F04D 29/30 415/206 |
| 2006/0278657 A1* | 12/2006 | Roatis | B67D 1/0079 222/129.1 |
| 2009/0044808 A1 | 2/2009 | Guney et al. | |
| 2009/0050156 A1 | 2/2009 | Ng et al. | |
| 2009/0301485 A1* | 12/2009 | Kenyon | F04D 29/30 416/182 |
| 2010/0000534 A1 | 1/2010 | Kooij et al. | |
| 2010/0008768 A1* | 1/2010 | Vedsted | F04D 7/04 415/173.1 |
| 2010/0059055 A1* | 3/2010 | Brungart | F04D 29/668 128/204.18 |
| 2011/0073110 A1 | 3/2011 | Kenyon et al. | |
| 2012/0045338 A1 | 2/2012 | Tadokoro et al. | |
| 2012/0195747 A1* | 8/2012 | Fukuda | F04D 29/441 415/206 |
| 2012/0285454 A1* | 11/2012 | Nibu | F04D 29/4246 128/204.18 |
| 2015/0044048 A1 | 2/2015 | Ahn | |
| 2016/0290355 A1 | 10/2016 | Lin | |
| 2016/0339193 A1 | 11/2016 | Daly et al. | |
| 2017/0082116 A1* | 3/2017 | Nibu | H01B 7/00 |
| 2019/0374732 A1 | 12/2019 | Cariola et al. | |
| 2020/0158126 A1* | 5/2020 | Nibu | H01B 7/02 |
| 2021/0190086 A1* | 6/2021 | Nibu | A61M 16/16 |

FOREIGN PATENT DOCUMENTS

| | | |
|---|---|---|
| CN | 102422025 A | 4/2012 |
| CN | 103352866 A | 10/2013 |
| CN | 104343726 A | 2/2015 |
| CN | 106151097 A | 11/2016 |
| FR | 3 001 897 A1 | 8/2014 |
| JP | 8-247092 A | 9/1996 |
| JP | 10-54389 A | 2/1998 |
| JP | 2000-34993 | 2/2000 |
| JP | 2000-104699 A | 4/2000 |
| JP | 2007-518933 A | 7/2007 |
| JP | 2009-537735 A | 10/2009 |
| JP | 2011-247096 A | 12/2011 |
| JP | 2015-510979 A | 4/2015 |
| JP | 2015-86827 A | 5/2015 |
| KR | 200447433 Y1 * | 1/2010 |
| WO | WO 98/004310 A1 | 2/1998 |
| WO | WO 98/034665 A1 | 8/1998 |
| WO | WO 99/64747 A1 | 12/1999 |
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2007/048206 A1 | 5/2007 |
| WO | WO 2009/052560 A1 | 4/2009 |
| WO | WO 2010/135785 A1 | 12/2010 |
| WO | WO 2012/171072 A1 | 12/2012 |
| WO | WO 2013/020167 A1 | 2/2013 |
| WO | WO 2017/046135 A1 | 3/2017 |

OTHER PUBLICATIONS

"Respiratory Physiology", by John B. West, Lippincott Williams & Wilkins, 9th edition published 2012, 8 pages.
International Search Report Mailed May 14, 2018 in International Application No. PCT/AU2018/050109, 4 pages.
Written Opinion of the International Searching Authority mailed May 14, 2018 in International Application No. PCT/AU2018/050109, 4 pages.
International Preliminary Report on Patentability mailed Aug. 20, 2019 in International Application No. PCT/AU2018/050109, 5 pages.
Notification of the First Office Action mailed Jun. 16, 2021 in Chinese Application No. 201880021416.8, with English translation, 12 pages.
Final Rejection mailed Apr. 18, 2022 in Japanese Application No. 2019-543852, with English translation, 5 pages.
Cariola et al., U.S. Appl. No. 16/485,591, filed Aug. 13, 2019, for "An Impeller for a Respiratory Device," (parent application).
Notice of Reasons for Refusal mailed Apr. 24, 2023 in Japanese Application No. 2022-128134, with English translation, 12 pages.
Notice of Reasons for Refusal mailed Jul. 16, 2024 in Japanese Application No. 2023-206979, with English translation, 7 pages.

* cited by examiner

IMPELLER FOR A RESPIRATORY DEVICE

1 CROSS-REFERENCE TO RELATED APPLICATIONS

This application is a continuation of U.S. application Ser. No. 16/485,591, filed Aug. 13, 2019, now allowed, which is the U.S. national phase of International Application No. PCT/AU2018/050109 filed Feb. 13, 2018, which designated the U.S. and claims the benefit of U.S. Provisional Application Nos. 62/458,862, filed Feb. 14, 2017, and 62/512,445, filed May 30, 2017, the entire contents of each of which are incorporated herein by reference.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

2 BACKGROUND OF THE TECHNOLOGY

2.1 Field of the Technology

The present technology relates to an impeller for a blower for a respiratory therapy device, such as a positive airway pressure (PAP) device or a ventilator. In an example, the blower may be used in a PAP device used for the delivery of respiratory therapy to a patient. More specifically, the impeller may be particularly suited for a small respiratory pressure therapy device, such as one designed to minimize a footprint, to be portable, or to be wearable.

2.2 Description of the Related Art

2.2.1 Therapy

Various therapies, such as Continuous Positive Airway Pressure (CPAP) therapy, Non-invasive ventilation (NIV) and Invasive ventilation (IV) have been used to treat one or more respiratory disorders.

2.2.2 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

2.2.2.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient.

2.2.2.2 Respiratory Pressure Therapy (RPT) Device

A respiratory pressure therapy (RPT) device may be used to deliver one or more of a number of therapies described above, such as by generating a flow of air for delivery to an entrance to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalized air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One suitable form of pressure generators for RPT devices may be a centrifugal air blower, which may comprise one or more impellers. A designer for an impeller may face challenges, as a designer of a device may be presented with an infinite number of choices to make.

For example, an impeller for an RPT device may have competing desirable properties such as high efficiency, flow rate and pressure output requirements for therapy, small size and rotational inertia, low cost, high mechanical strength and durability. In meeting one, for instance, by simply reducing a diameter of an existing impeller, its maximum available flow rate may be decreased, while its size and inertia are advantageously decreased. Some aerodynamic features for example may improve an efficiency of the impeller, however may increase its costs as the required manufacturing process becomes more complicated.

Simply put, design criteria often conflict, meaning that certain design choices are far from routine or inevitable.

3 BRIEF SUMMARY OF THE TECHNOLOGY

The present technology is directed towards providing medical devices comprising alternative arrangements of impellers, blowers and/or RPT devices that may ameliorate or reduce some of the known challenges in the art, and manufacturing methods thereof, thus having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to an RPT device having a reduced or compact size (e.g., impeller with a reduced size), while minimizing any compromises to noise and/or efficiency.

Another aspect of the present technology relates to a compact respiratory therapy device suitable for use by a patient during sleep to provide respiratory pressure therapy such as at a pressure between 4-30 cmH$_2$O. The device includes a housing, an inlet, an outlet, a motor including a rotor, and an impeller configured to be rotated by the rotor to deliver a flow of air from the inlet toward the outlet. The impeller includes a set of impeller blades, each impeller blade including a leading edge and a trailing edge. The impeller also includes a first shroud and a second shroud, each shroud at least partly defining a flow passage through the impeller. The first shroud includes a wall defining a periphery of an impeller inlet. The compact respiratory therapy device is configured to deliver the flow of air from the outlet for delivery to the patient at a pressure between 4-30 cmH$_2$O at an overall sound power level of less than 50 dB(A) thereby reducing any disturbance to a quality of sleep for the patient. A diameter of the impeller is less than 50 mm. The first shroud and the second shroud are configured such that the flow passage is narrower in an axial direction at an outer portion of the impeller than at an inner portion of the impeller, and a diameter of the impeller inlet is at least 50% of the diameter of the impeller.

In an example, the first shroud may be substantially non-planar. In an example, the first shroud may include a frusto-conical shape. In an example, the second shroud may be substantially planar. In an example, the leading edge may be inclined by an angle greater than 45 degrees with respect to an axis of the motor. In an example, the impeller may comprise a metal. In an example, the impeller may be manufactured by an additive process. In an example, the impeller may comprise a first moulded portion and a second moulded portion fastened together. In an example, the first moulded portion may comprise the first shroud and the set of impeller blades. In an example, the second moulded portion may comprise an impeller hub and the second shroud. In an example, the first moulded portion and the second moulded portion may be fastened together by a snap fit.

Another aspect of the present technology relates to a compact respiratory therapy device suitable for use by a patient during sleep to provide respiratory pressure therapy such as at a pressure between 4-30 cmH$_2$O. The device includes a housing, an inlet, an outlet, a motor including a rotor, and an impeller configured to be rotated by the rotor to deliver a flow of air from the inlet toward the outlet. The impeller includes a set of impeller blades, each impeller blade comprising a leading edge and a trailing edge. The impeller also includes a first shroud and a second shroud, each shroud at least partly defining a flow passage through the impeller. The first shroud includes a wall defining a periphery of an impeller inlet. The compact respiratory therapy device is configured to deliver the flow of air from the outlet for delivery to the patient at a pressure between 4-30 cmH$_2$O at an overall sound power level of less than 50 dB(A) thereby reducing any disturbance to a quality of sleep for the patient. A diameter of the impeller is less than 50 mm. A thickness of the leading edge and the trailing edge of each impeller blade is less than about 0.2 mm to improve efficiency of the compact respiratory therapy device.

In an example, the impeller may comprise a metal. In an example, the impeller may be produced by an additive method. In an example, the first shroud may be tapered in a radial direction with respect to an axial direction. In an example, the rotor may include a shaft comprising the same metal as the impeller. In an example, the leading edge and the trailing edge of each impeller blade may comprise an elastomer. In example, each impeller blade may further comprise a rigid material. In an example, the thickness of the leading edge and the trailing edge of each impeller blade may be less than 0.1 mm.

Another aspect of the present technology relates to a compact respiratory therapy device suitable for use by a patient during sleep to provide respiratory pressure therapy. The device includes a housing, an inlet, an outlet, a motor including a rotor, and an impeller configured to be rotated by the rotor to deliver a flow of air from the inlet toward the outlet. The impeller includes a plurality of impeller blades, each impeller blade comprising a leading edge and a trailing edge. The impeller also includes a first shroud and a second shroud, each shroud at least partly defining a flow passage through the impeller. The first shroud includes a wall defining a periphery of an impeller inlet. The compact respiratory therapy device is configured to deliver the flow of air from the outlet for delivery to the patient at a pressure between 4-30 cm$_2$O at an overall sound power level of less than 50 dB(A) thereby reducing any disturbance to a quality of sleep for the patient. A diameter of the impeller is less than 50 mm, and a leading edge of the periphery of the impeller inlet comprises a cross sectional shape with a radius of at least 0.5 mm, whereby in use, an air flow entering the impeller is discouraged from detachment at or around the radius.

Another aspect of the present technology relates to a compact respiratory therapy device suitable for use by a patient during sleep to provide respiratory pressure therapy. The device includes a housing, an inlet, an outlet, a motor including a rotor, and an impeller configured to be rotated by the rotor to deliver a flow of air from the inlet toward the outlet. The impeller includes a plurality of impeller blades, each impeller blade comprising a leading edge and a trailing edge. The impeller also includes a first shroud and a second shroud, each shroud at least partly defining a flow passage through the impeller. The first shroud includes a wall defining a periphery of an impeller inlet. The compact respiratory therapy device is configured to deliver the flow of air from the outlet for delivery to the patient at a pressure between 4-30 cm$_2$O at an overall sound power level of less than 50 dB(A) thereby reducing any disturbance to a quality of sleep for the patient. A diameter of the impeller is less than about 50 mm, and a leading edge of the first shroud comprises a cross sectional shape with a radius of at least 0.5 mm, whereby in use, an air flow entering the impeller is discouraged from detachment.

In an example, the radius of the leading edge of the first shroud may be greater than 70% of a maximum thickness of a body of the first shroud. In an example, the radius of the leading edge of the first shroud may be greater than the maximum thickness of the body of the first shroud. In an example, the first shroud may be tapered in an axial direction of the motor. In an example, the first shroud may comprise a frusto-conical shape. In an example, the second shroud may be substantially planar.

Another aspect of the present technology relates to a compact respiratory therapy device suitable for use by a patient during sleep to provide respiratory pressure therapy. The device includes a housing, an inlet, an outlet, a motor including a rotor, and an impeller configured to be rotated by the rotor to deliver a flow of air from the inlet toward the outlet. The impeller includes a plurality of impeller blades, each impeller blade comprising a leading edge and a trailing edge. The impeller also includes a first shroud and a second shroud, each shroud at least partly defining a flow passage through the impeller. The first shroud includes a wall defining a periphery of an impeller inlet. The compact respiratory therapy device is configured to deliver the flow of air from the outlet for delivery to the patient at a pressure between 4-30 cm$_2$O at an overall sound power level of less than 50 dB(A) thereby reducing any disturbance to a quality of sleep for the patient. A diameter of the impeller is less than about 50 mm, and a leading edge of the first shroud comprises a cross sectional shape with a radius of at least 1% of the diameter of the impeller, whereby in use, an air flow entering the impeller is discouraged from detachment.

Another aspect of the present technology relates to a compact respiratory therapy device suitable for use by a patient during sleep to provide respiratory pressure therapy. The device includes a housing, an inlet, an outlet, a motor including a rotor, and an impeller configured to be rotated by the rotor to deliver a flow of air from the inlet toward the outlet. The impeller includes a plurality of impeller blades, each impeller blade comprising a leading edge and a trailing edge. The impeller also includes a first shroud and a second shroud, each shroud at least partly defining a flow passage through the impeller. The first shroud includes a wall defining a periphery of an impeller inlet. The compact respiratory therapy device is configured to deliver the flow of air from the outlet for delivery to the patient at a pressure between 4-30 cmH$_2$O at an overall sound power level of less than 50 dB(A) thereby reducing any disturbance to a quality of sleep for the patient. A diameter of the impeller is less than about 50 mm, and the first shroud comprises a first material and the second shroud comprises a second material, where one of the first and second materials is an elastomer.

In an example, one of the first and second materials may be silicone. In an example, the plurality of impeller blades may comprise silicone at the trailing edge. In an example, the trailing edge may comprise serrations arranged along the trailing edge. In an example, the first shroud may be substantially non-planar. In an example, the first shroud may comprises a frusto-conical shape. In an example, the second shroud may be substantially planar. In an example, the leading edge may be inclined by an angle greater than 45 degrees with respect to an axis of the motor.

Another aspect of the present technology relates to a compact respiratory therapy device suitable for use by a patient during sleep to provide respiratory pressure therapy. The device includes a housing, an inlet, an outlet, a motor including a rotor, and an impeller configured to be rotated by the rotor to deliver a flow of air from the inlet toward the outlet. The impeller includes a first moulded part comprising a plurality of impeller blades, each impeller blade comprising a leading edge and a trailing edge, and a first shroud comprising a wall defining a periphery of an impeller inlet. The impeller also includes a second moulded part comprising a hub structured for coupling to the rotor and a second shroud. The compact respiratory therapy device is configured to deliver the flow of air from the outlet for delivery to the patient at a pressure between 4-30 cmH$_2$O at an overall sound power level of less than 50 dB(A) thereby reducing any disturbance to a quality of sleep for the patient. A diameter of the impeller is less than about 50 mm, and each shroud at least partly defines a flow passage through the impeller.

In an example, the first moulded part and the second moulded part may be fastened by a snap fit. In an example, the hub may be press fit onto the rotor and the snap fit may be tightened by the press fit. In an example, the first moulded part and the second moulded part may be welded together. In an example, the first moulded part may further comprise an outer portion of the second shroud, and the second moulded part may further comprise an outer portion of the first shroud. In an example, the second moulded part may further comprise inner portions of the impeller blades. In an example, the inner portions of the impeller blades may be adapted to be received in corresponding openings provided within the impeller blades. In an example, the first moulded part may comprise silicone. In an example, the first moulded part may be overmoulded to the second moulded part.

Another aspect of the present technology relates to a compact respiratory therapy device suitable for use by a patient during sleep to provide respiratory pressure therapy. The device includes a housing, an inlet, an outlet, a motor including a rotor, and an impeller configured to be rotated by the rotor to deliver a flow of air from the inlet toward the outlet. The impeller includes: a first moulded part including a plurality of impeller blades, each impeller blade including a leading edge and a trailing edge; a hub structured for coupling to the rotor; and a first shroud comprising a wall defining a periphery of an impeller inlet. The impeller further includes a second moulded part including: a second shroud; and a fastening portion. The compact respiratory therapy device is configured to deliver the flow of air from the outlet for delivery to the patient at a pressure between 4-30 cmH$_2$O at an overall sound power level of less than 50 dB(A) thereby reducing any disturbance to a quality of sleep for the patient. A diameter of the impeller is less than about 50 mm, and each shroud at least partly defines a flow passage through the impeller.

In an example, the first moulded part may further comprise a plurality of protrusions adapted to engage with the fastening portion of the second moulded part. In an example, each impeller blade may comprise a thickened protrusion adapted to engage with the fastening portion of the second moulded part. In an example, the fastening portion of the second moulded part may comprise a lower portion of the hub with which the hub of the first moulded part is adapted to engage.

Another aspect of the present technology relates to a compact respiratory therapy device suitable for use by a patient during sleep to provide respiratory pressure therapy. The device includes a housing, an inlet, an outlet, a motor including a rotor, and an impeller configured to be rotated by the rotor to deliver a flow of air from the inlet toward the outlet. The impeller includes: a first moulded part including a first shroud including a wall defining a periphery of an impeller inlet; a second moulded part including: a hub structured for coupling to the rotor, and a second shroud; and a third moulded part comprising a plurality of impeller blades, each impeller blade comprising a leading edge and a trailing edge. The compact respiratory therapy device is configured to deliver the flow of air from the outlet for delivery to the patient at a pressure between 4-30 cmH$_2$O at an overall sound power level of less than 50 dB(A) thereby reducing any disturbance to a quality of sleep for the patient. A diameter of the impeller is less than about 50 mm, and each shroud at least partly defines a flow passage through the impeller.

Another aspect of the present technology relates to a compact respiratory therapy device suitable for use by a patient during sleep to provide respiratory pressure therapy. The device includes a housing, an inlet, an outlet, a motor including a rotor, and an impeller configured to be rotated by the rotor to deliver a flow of air from the inlet toward the outlet. The impeller includes: a first moulded part including: a first shroud comprising a wall defining a periphery of an impeller inlet; and a plurality of impeller blades, each impeller blade comprising a leading edge and a trailing edge; a second moulded part comprising a second shroud; and a third moulded part comprising a hub structured for coupling to the rotor. The compact respiratory therapy device is configured to deliver the flow of air from the outlet for delivery to the patient at a pressure between 4-30 cmH$_2$O at an overall sound power level of less than 50 dB(A) thereby reducing any disturbance to a quality of sleep for the patient. A diameter of the impeller is less than about 50 mm, and each shroud at least partly defines a flow passage through the impeller.

In an example, the second moulded part may further comprise a lower portion of the hub and lower portions of each of the impeller blades. In an example, the first moulded part may further comprise an upper portion of the hub. In an example, the third moulded part may be injection moulded to the first and second moulded parts to fasten the first and second moulded parts to one another.

Another aspect of the present technology relates to an impeller configured to be rotated by a rotor to deliver a flow of air. The impeller includes: a set of impeller blades, each impeller blade comprising a leading edge and a trailing edge; and a first shroud and a second shroud, each shroud at least partly defining a flow passage through the impeller, the first shroud comprising a wall defining a periphery of an impeller inlet. A diameter of the impeller is less than 50 mm. The impeller comprises a metallic material, and the impeller is manufactured by an additive process.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

4.2 Respiratory System And Facial Anatomy

FIG. 2A shows an overview of a human respiratory system including the nasal and oral cavities, the larynx, vocal folds, oesophagus, trachea, bronchus, lung, alveolar sacs, heart and diaphragm.

4.3 Patient Interface

FIG. 3A shows a patient interface in the form of a nasal mask in accordance with one form of the present technology.

4.4 RPT Device

FIG. 4A shows an RPT device in accordance with one form of the present technology.

4.5 Impeller

Figure 5A:
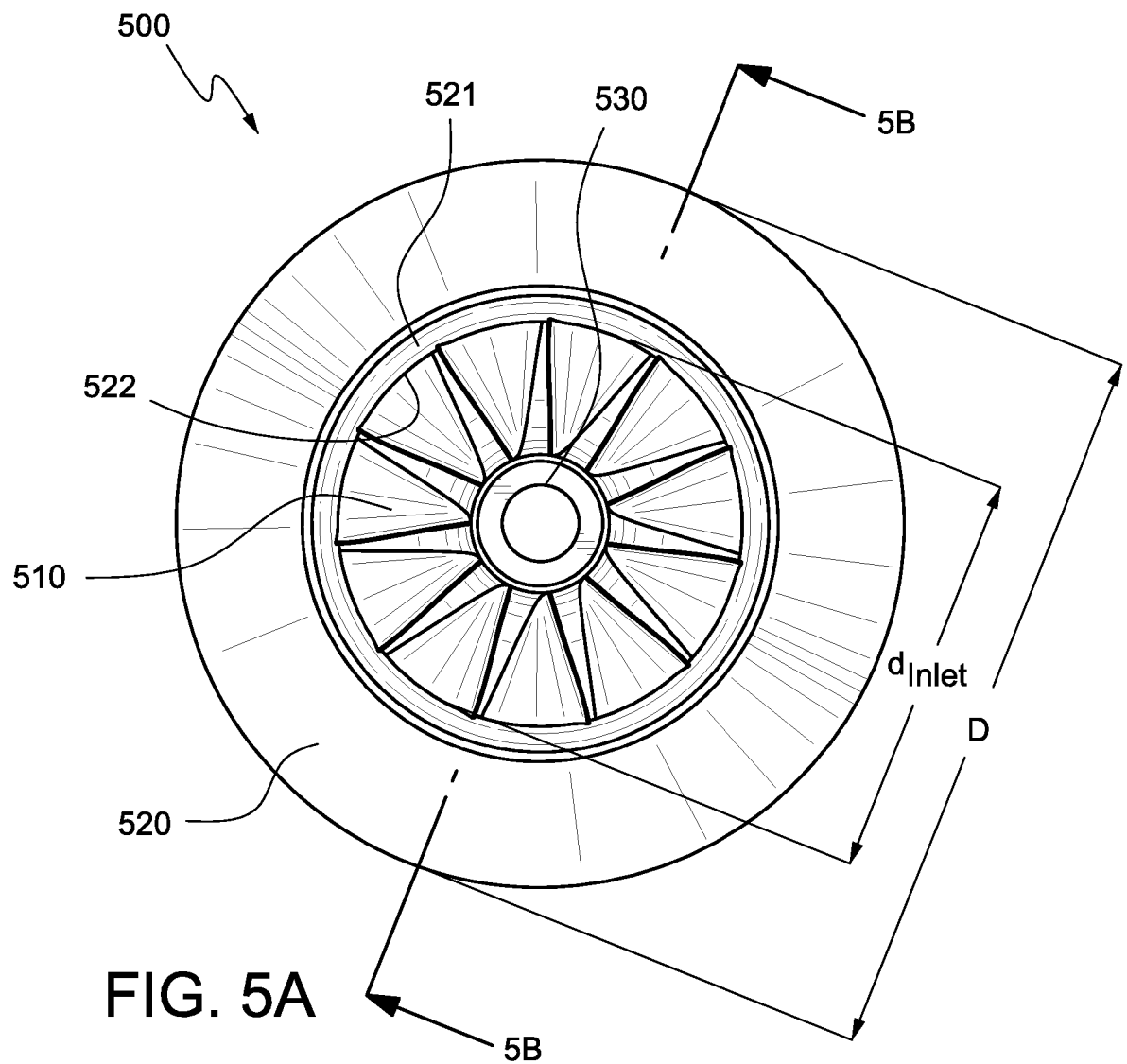
FIG. 5A shows an impeller in accordance with one form of the present technology.
Figure 5B:
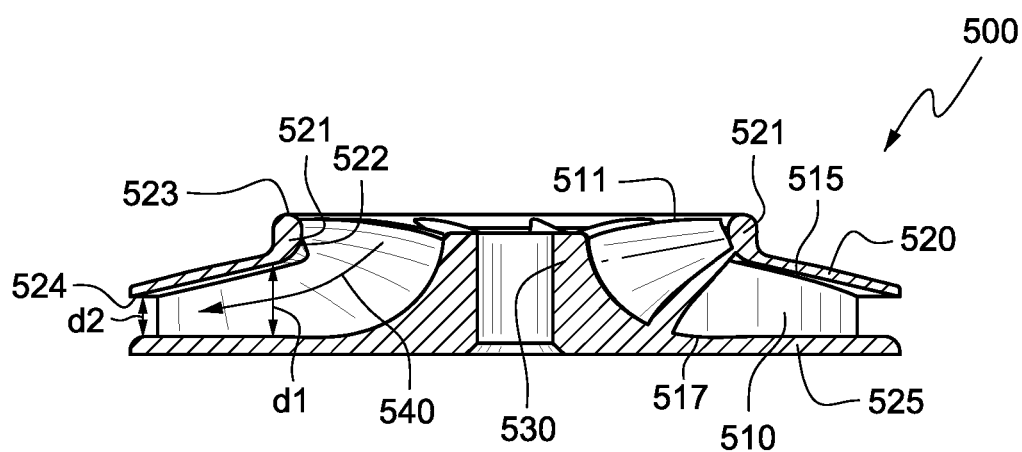
FIG. 5B shows a cross-section of the impeller shown in FIG. 5A.
Figure 5C:
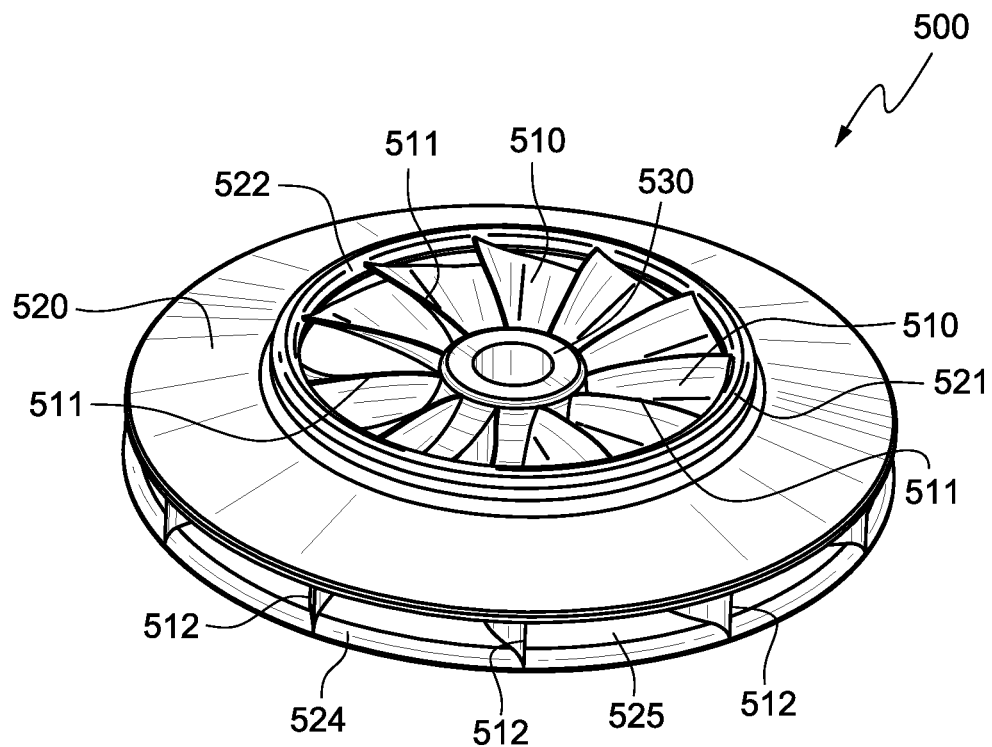
FIG. 5C shows an isometric view of the impeller shown in FIG. 5A.
Figure 5D:
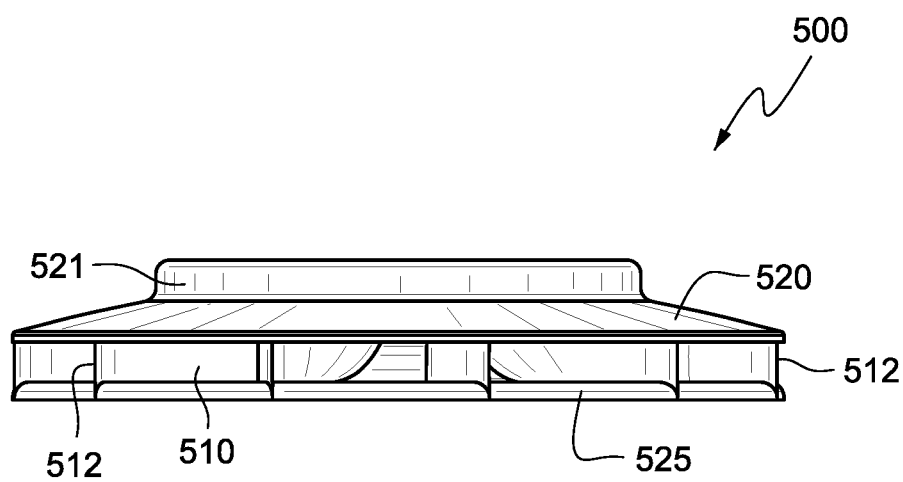
FIG. 5D shows an elevation view of the impeller shown in FIG. 5A.
Figure 5E:
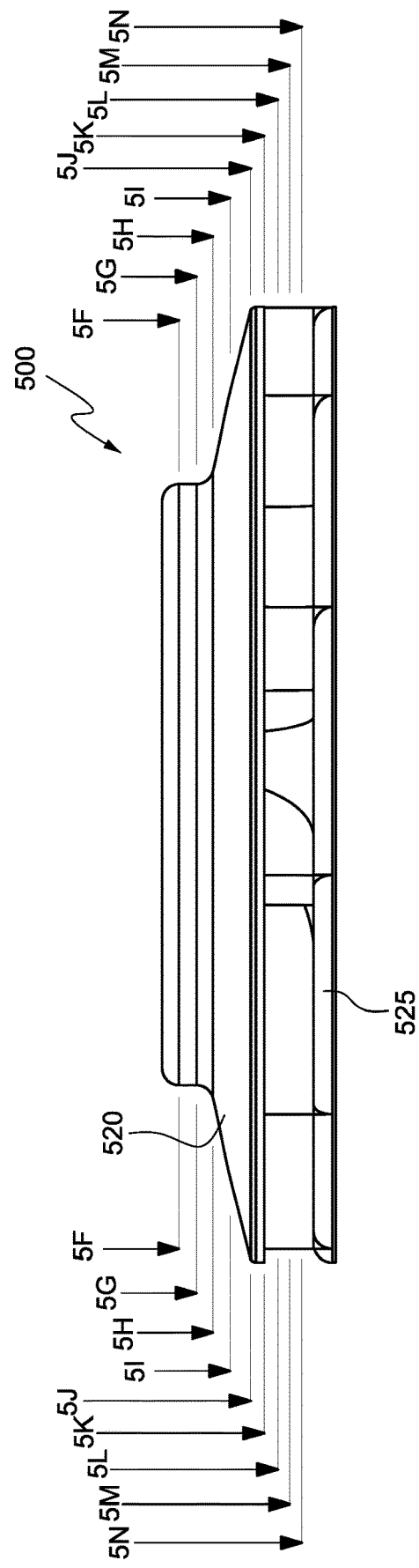
FIG. 5E shows an elevation view of the impeller shown in FIG. 5A, indicating cross sections taken for FIGS. 5F-5N.
Figure 5F:
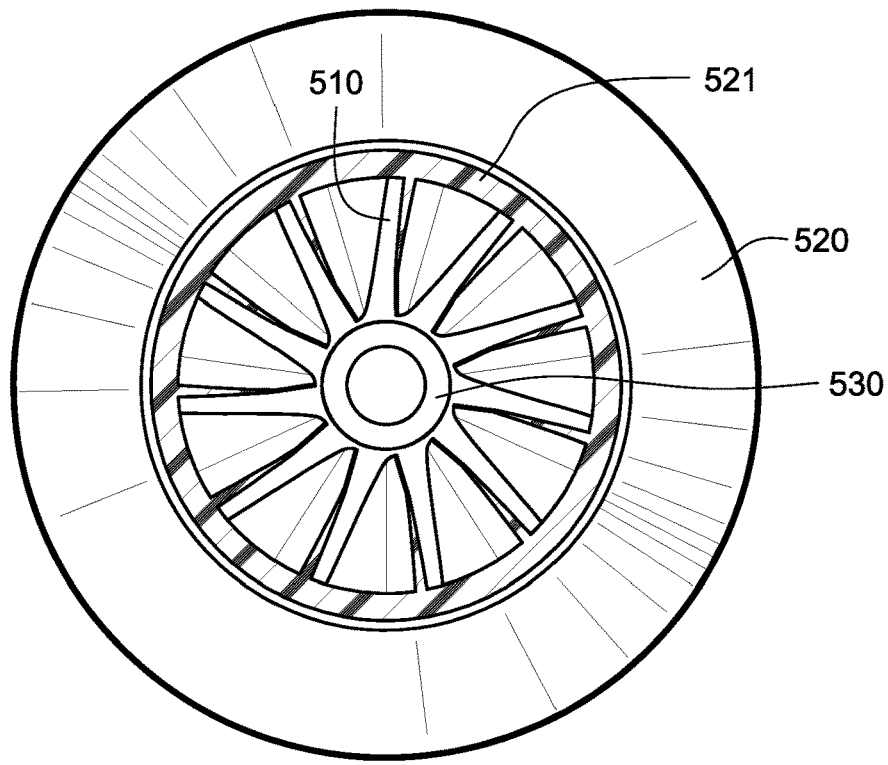
FIGS. 5F-5N show plan views of an impeller in accordance with one form of the present technology at various cross sections as indicated on FIG. 5E.
Figure 5G:
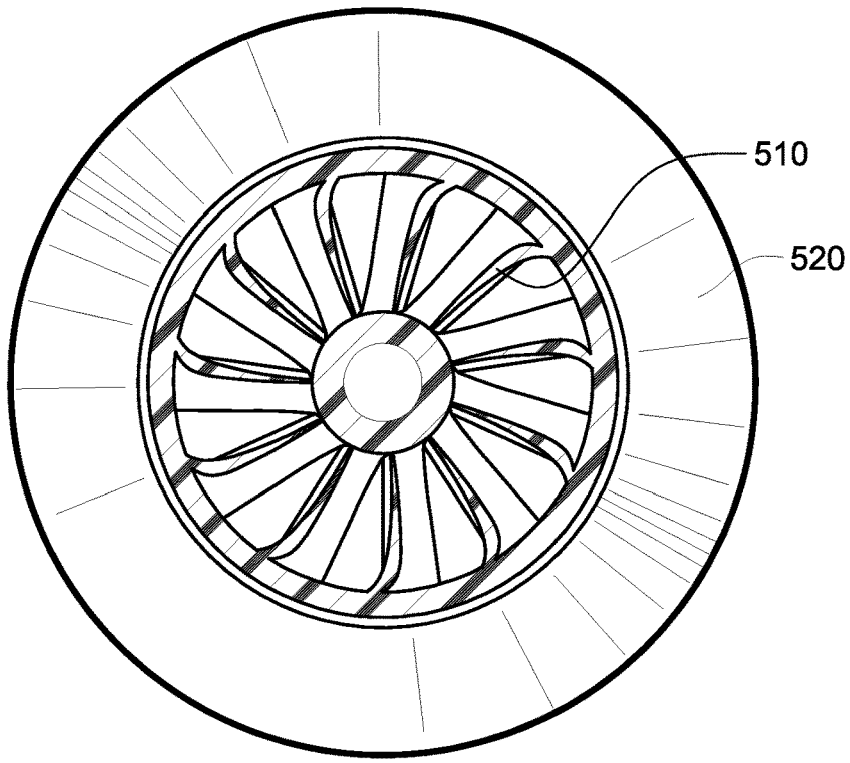
Figure 5H:
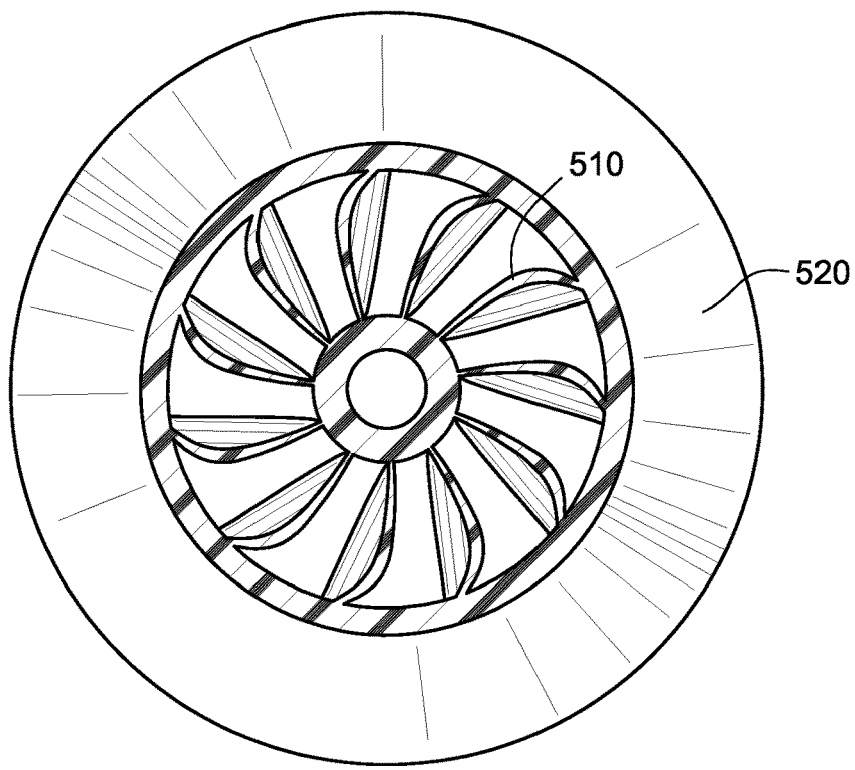
Figure 5I:
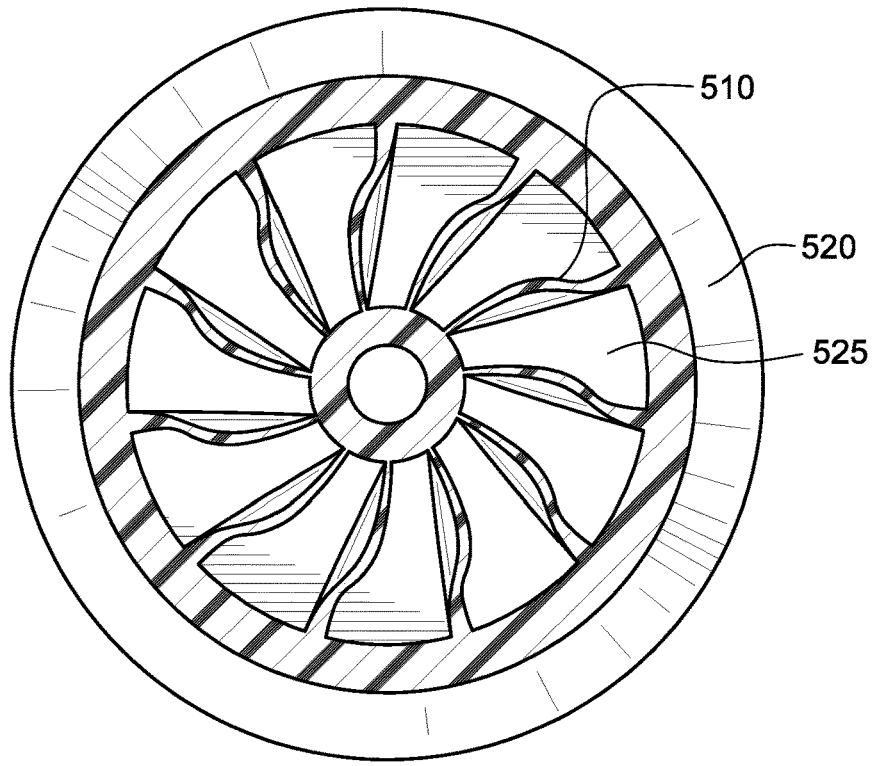
Figure 5J:
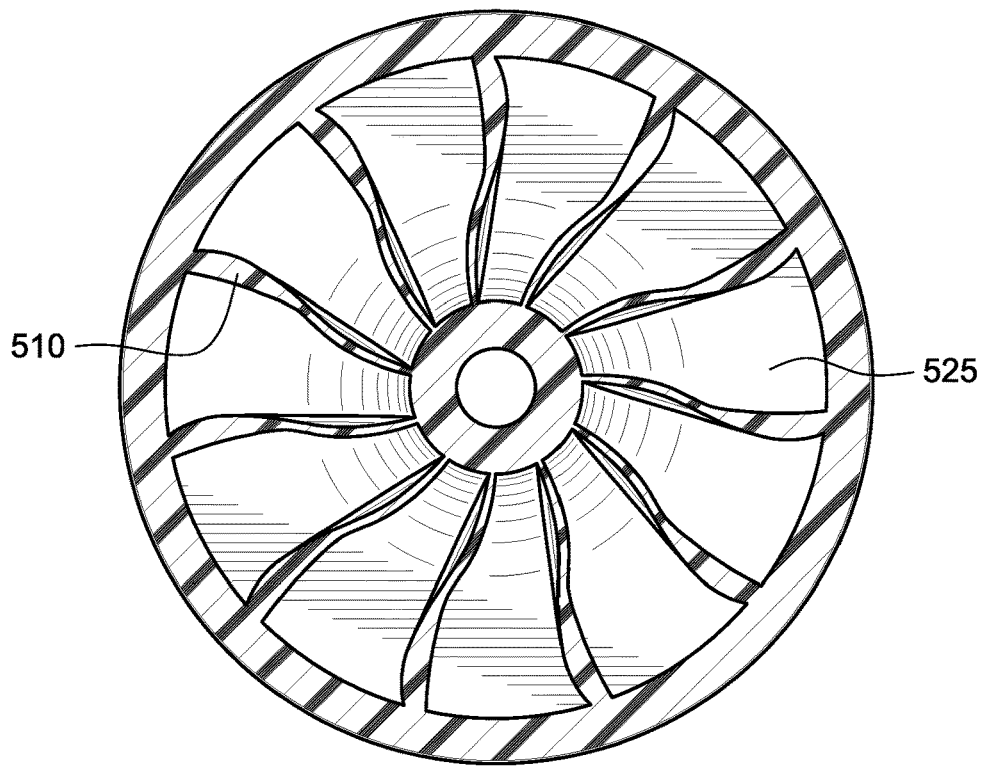
Figure 5K:
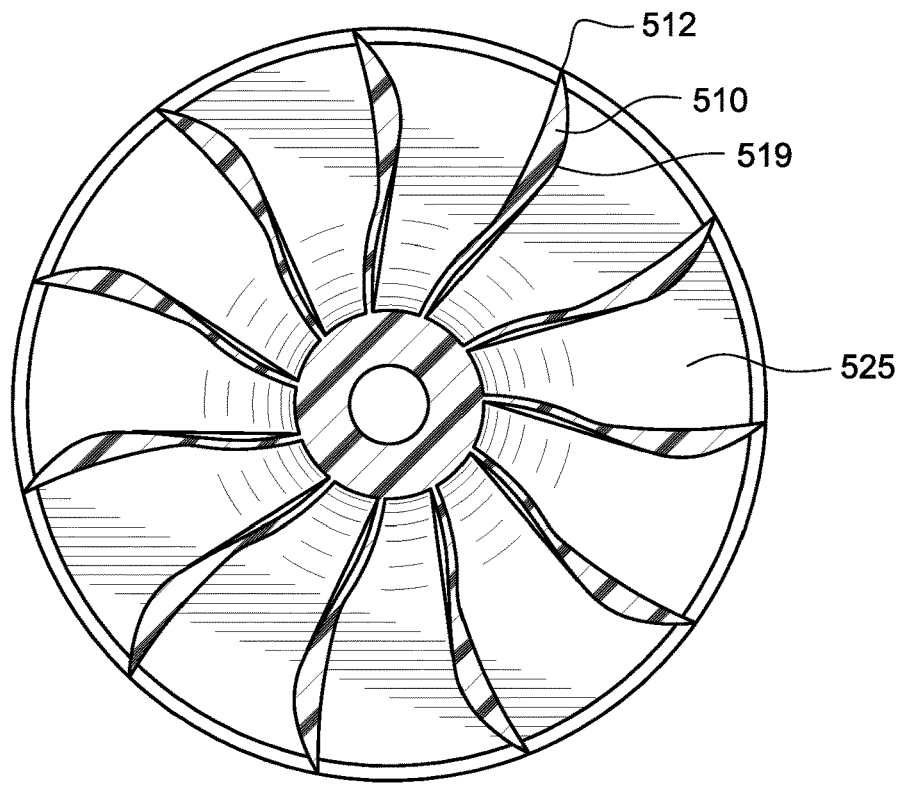
Figure 5L:
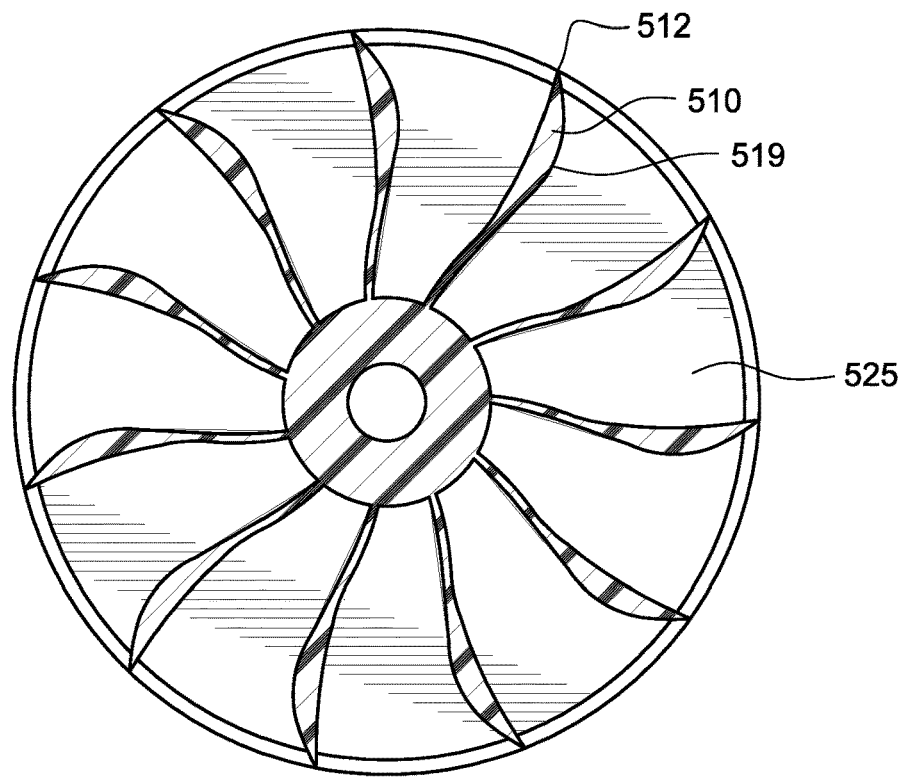
Figure 5M:
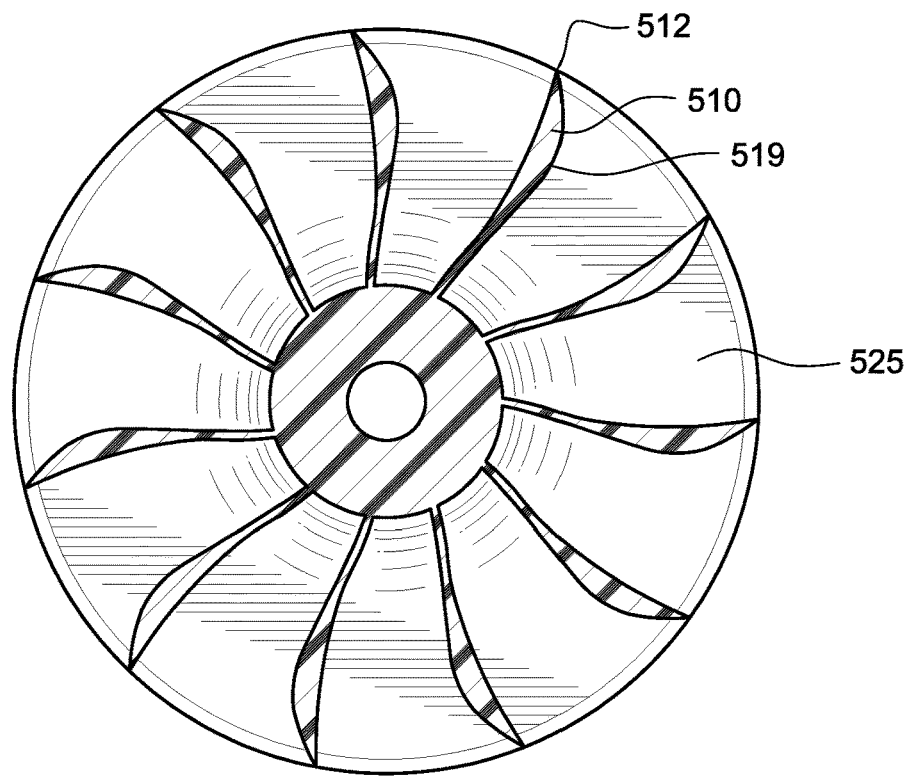
Figure 5N:
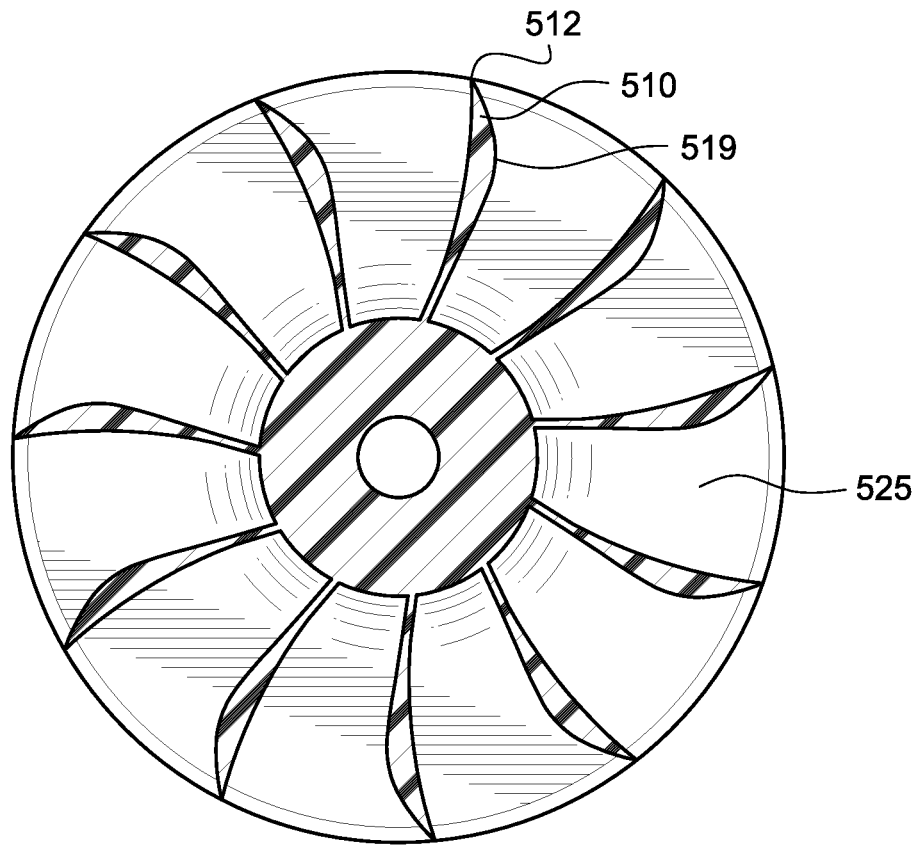
Figure 5O:
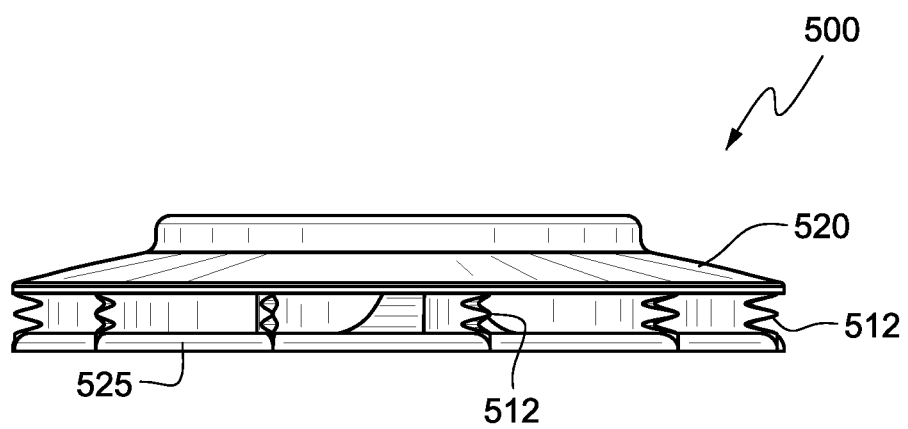
FIG. 5O shows an elevation view of an impeller in accordance with one form of the present technology.
Figure 5P:
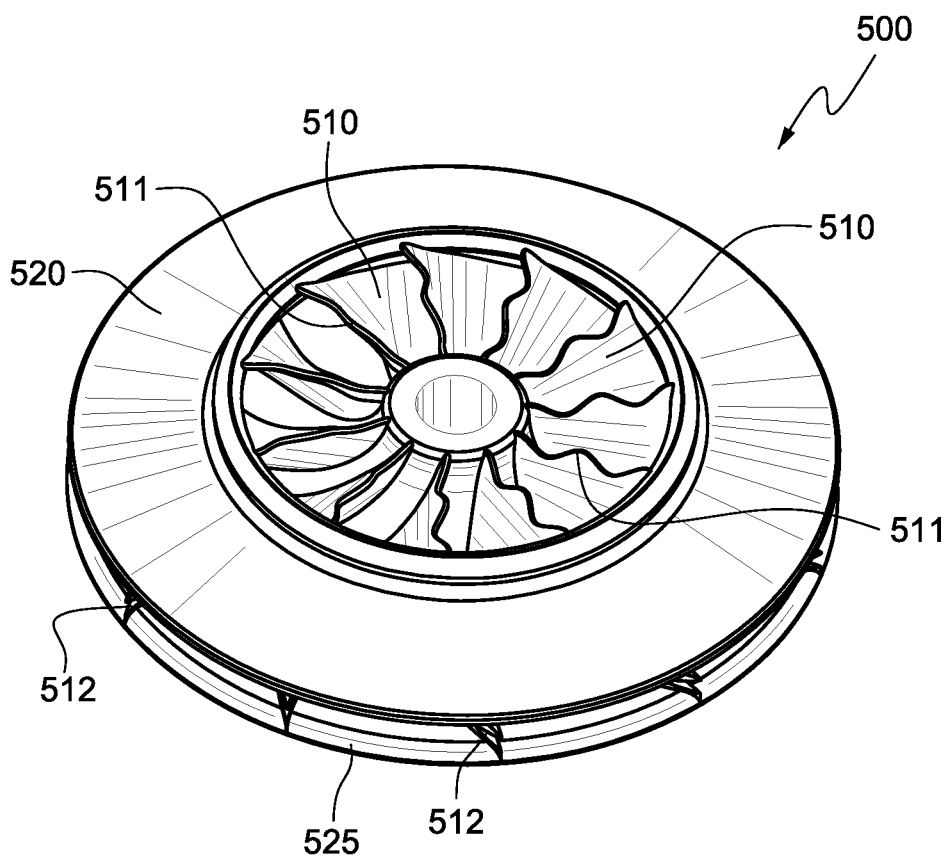
FIG. 5P shows an isometric view of the impeller shown in FIG. 5O.
Figure 5Q:
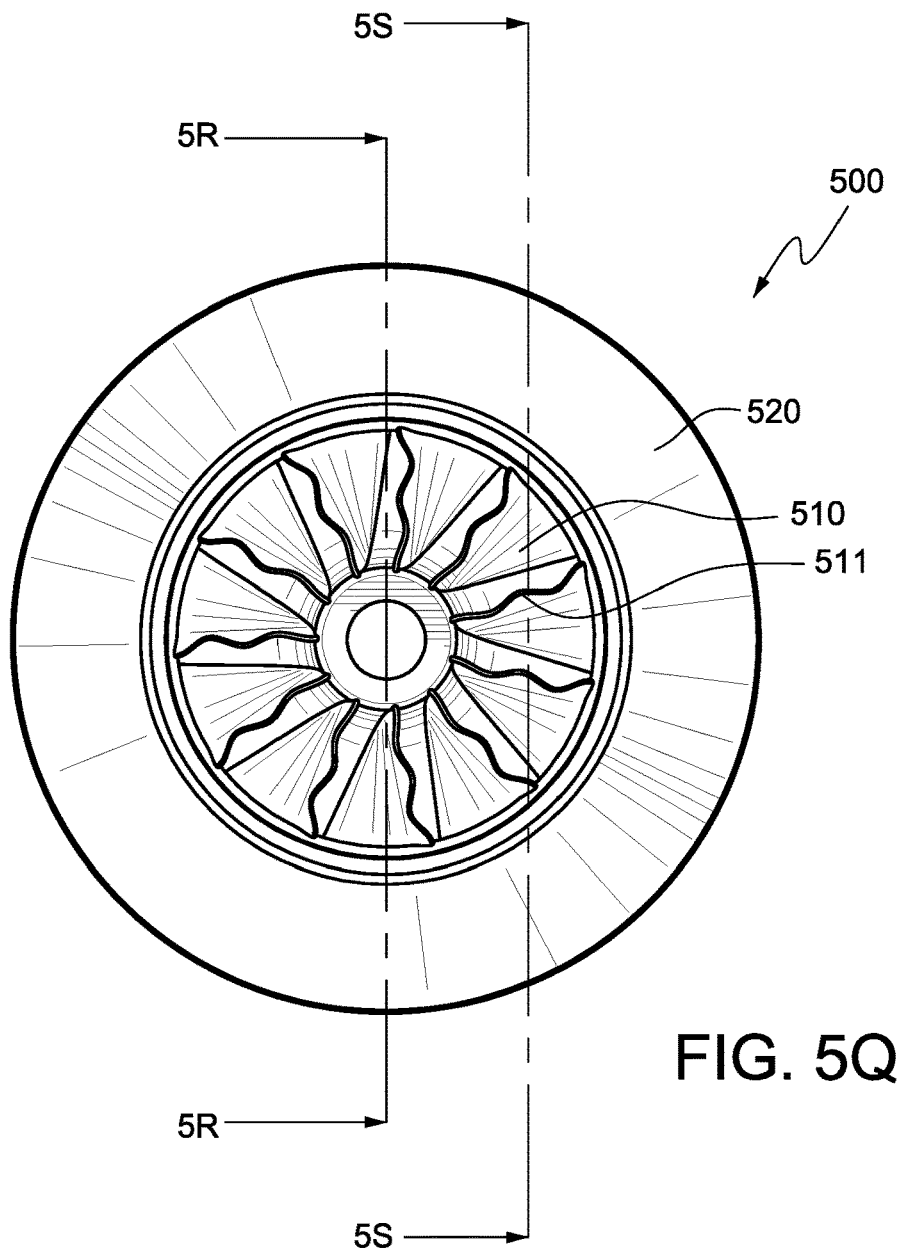
FIG. 5Q shows a plan view of the impeller shown in FIG. 5O, indicating cross-sections taken for FIGS. 5R-5S.
Figure 5R:
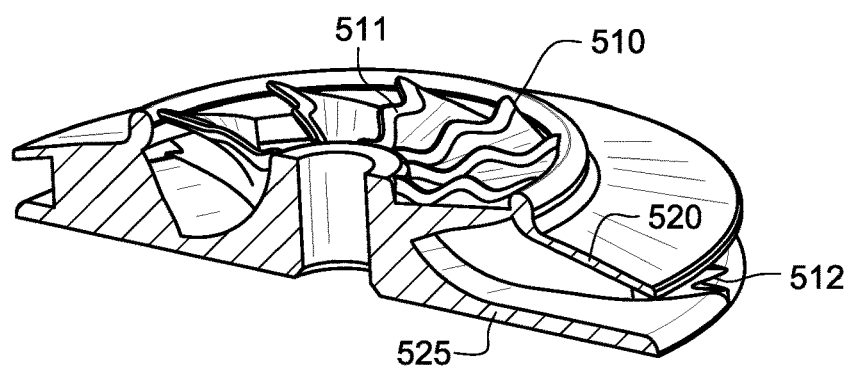
FIGS. 5R-5S show cross-sections of the impeller as indicated on FIG. 5Q.
Figure 5S:
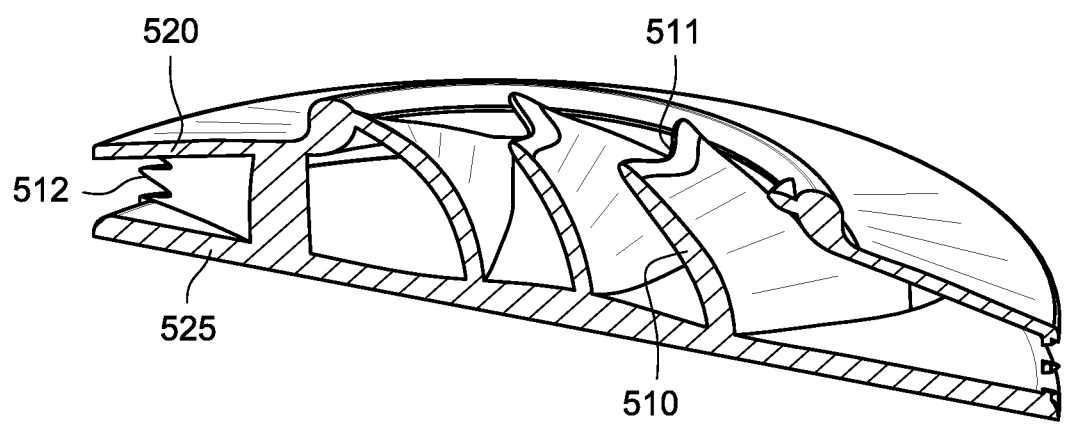
Figure 5T:
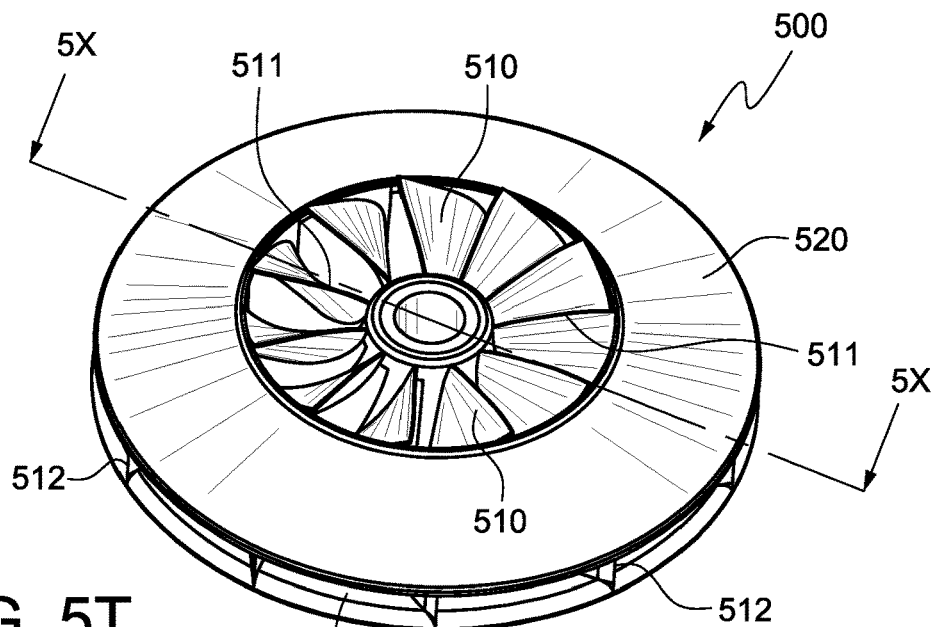
FIG. 5T shows an isometric view of an impeller in accordance with one form of the present technology.
Figure 5U:
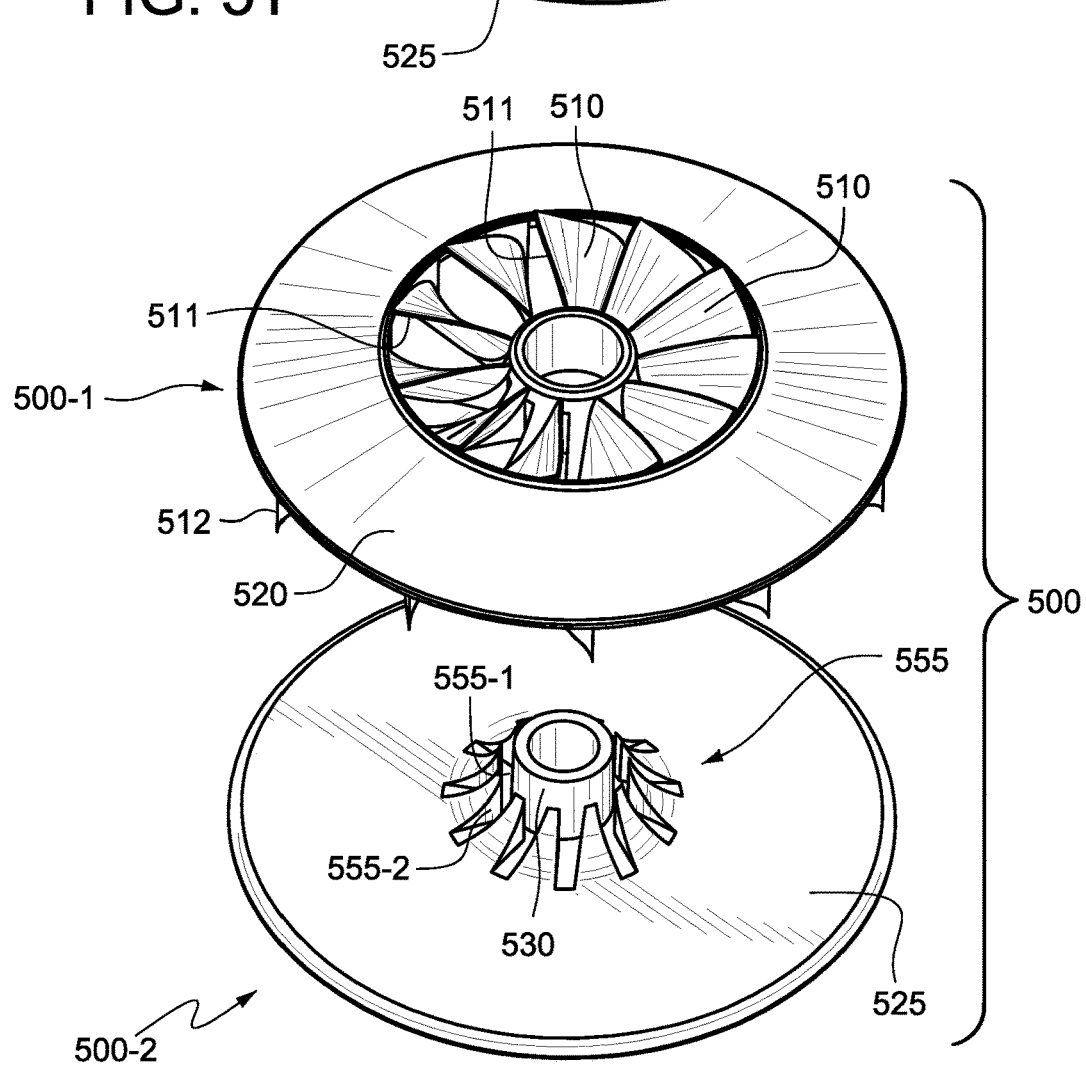
FIG. 5U shows an exploded view of the impeller shown in FIG. 5T.
Figure 5V:
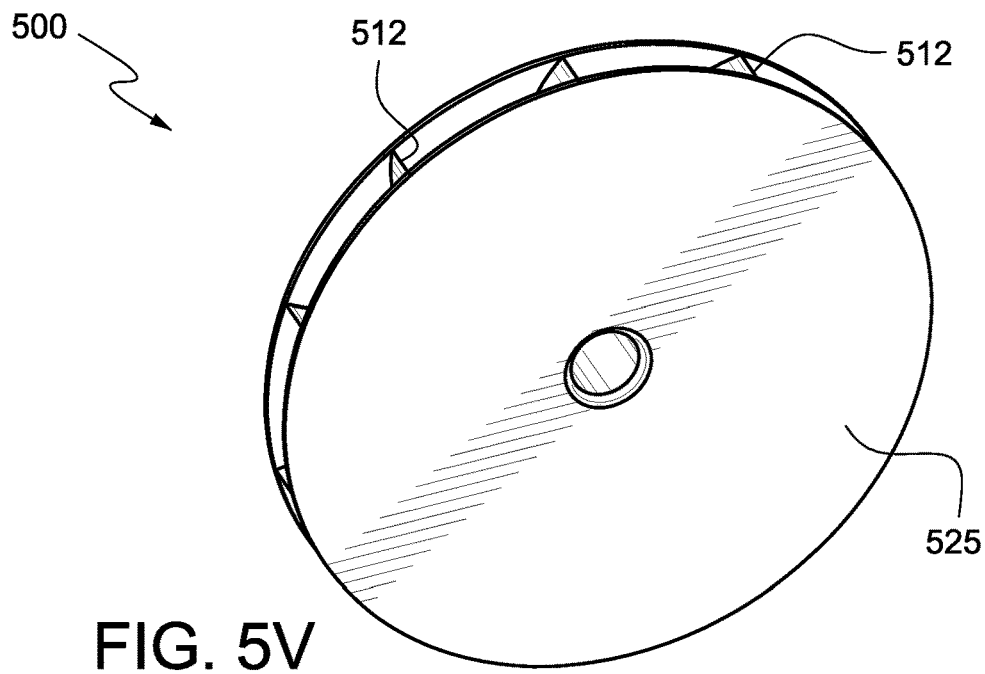
FIG. 5V shows a bottom isometric view of the impeller shown in FIG. 5T.
Figure 5W:
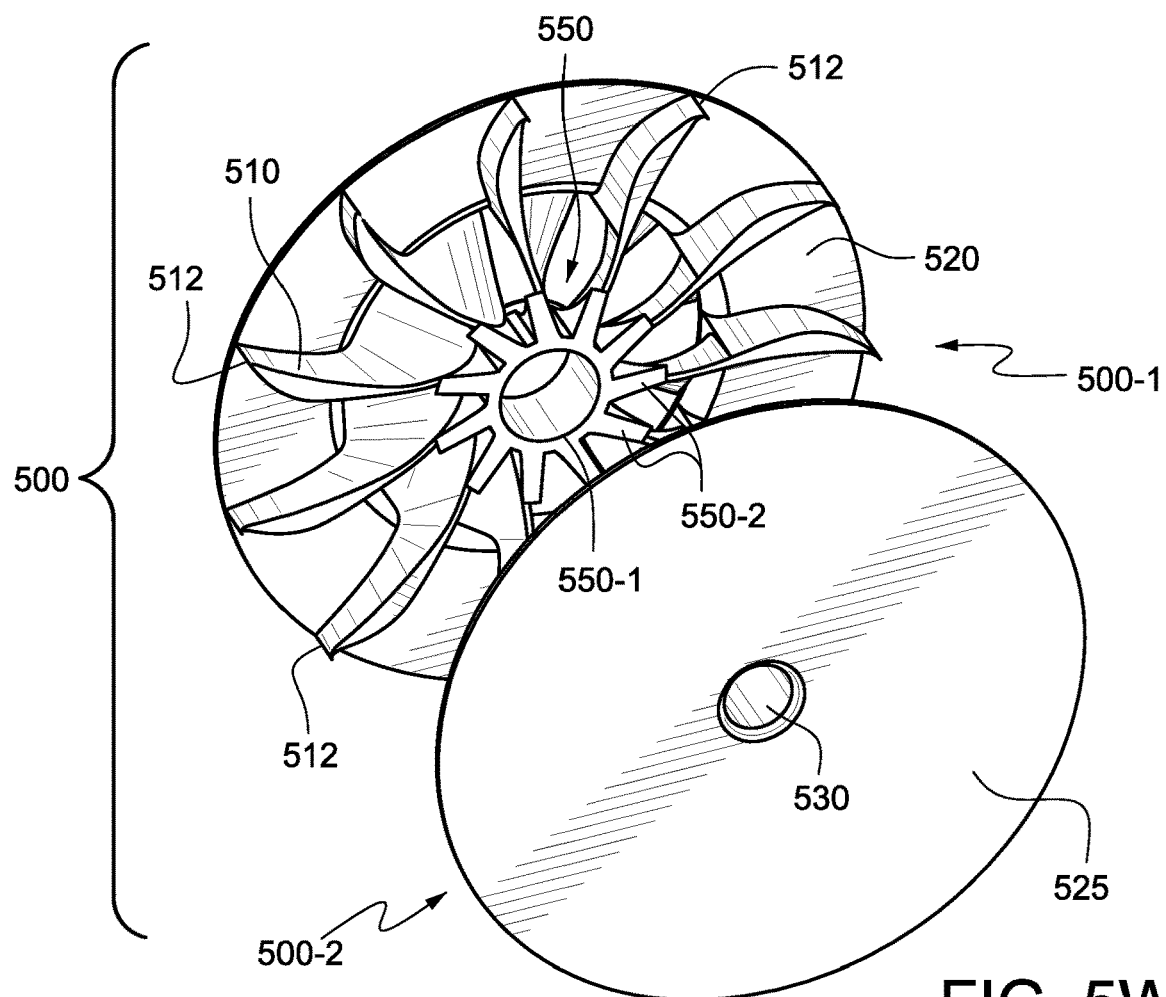
FIG. 5W shows an exploded view of the impeller shown in FIG. 5V.
Figure 5X:
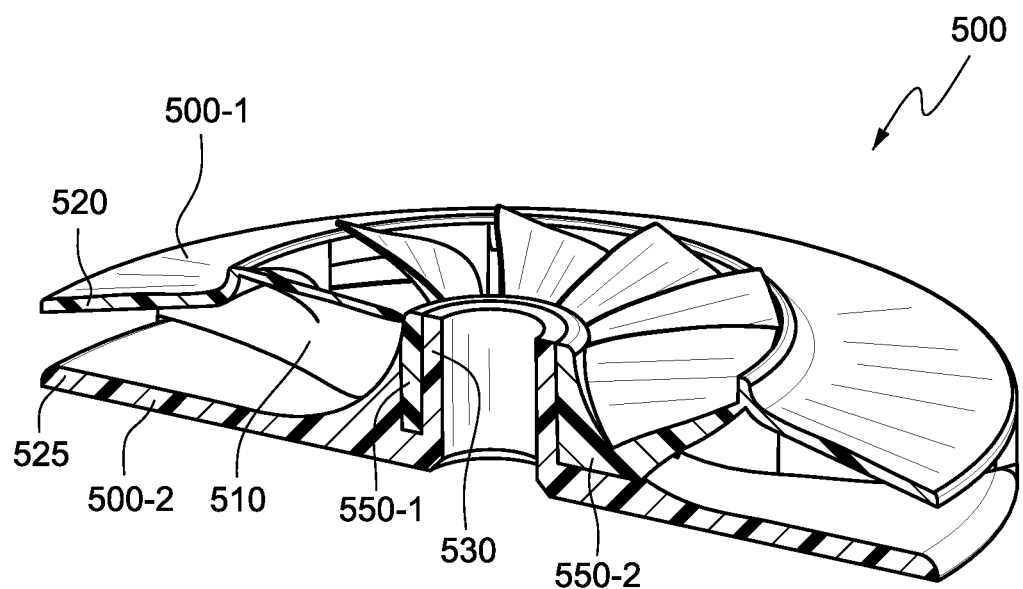
FIG. 5X shows a cross-section of the impeller as indicated on FIG. 5T.
Figure 5Y:
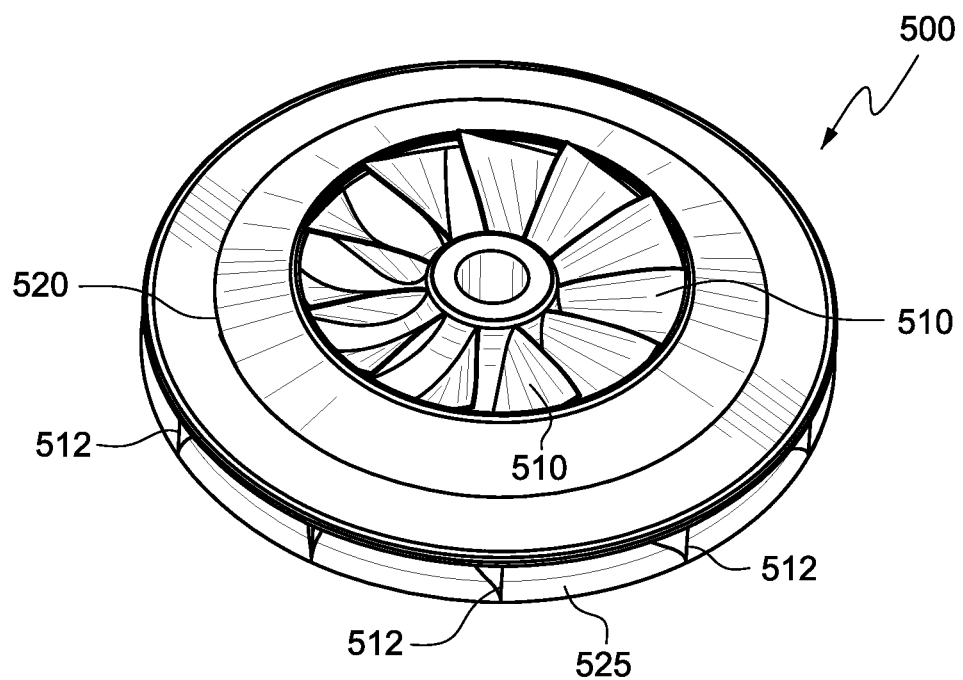
FIG. 5Y shows an isometric view of an impeller in accordance with one form of the present technology.
Figure 5Z:
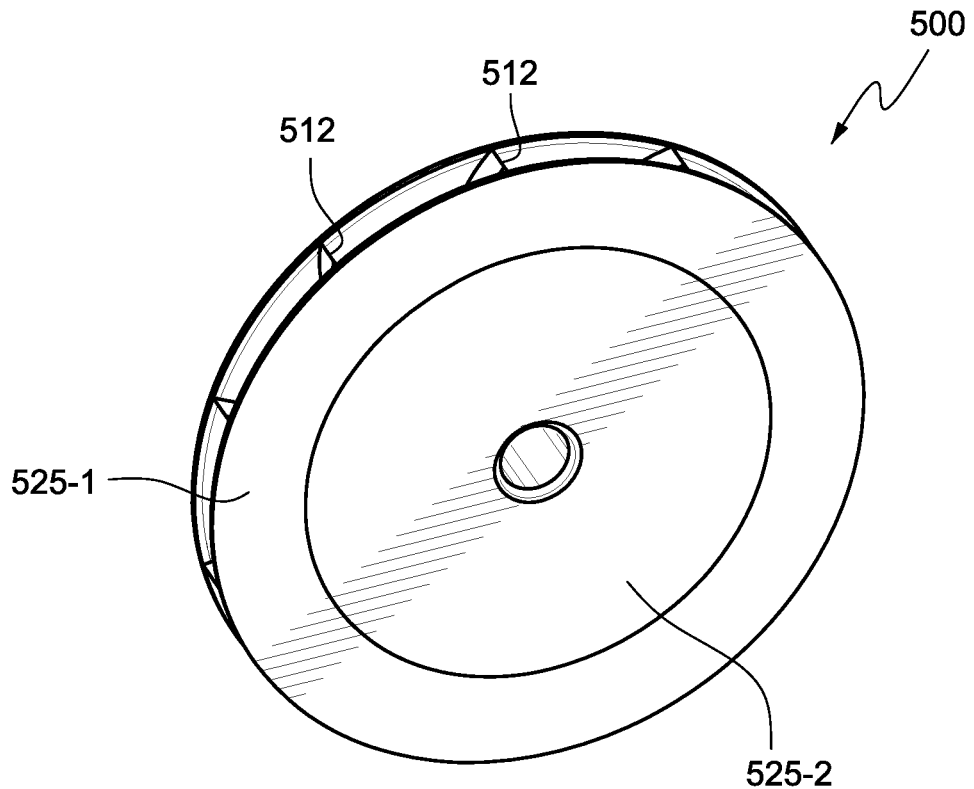
FIG. 5Z shows a bottom isometric view of the impeller shown in FIG. 5Y.
Figure 5A:
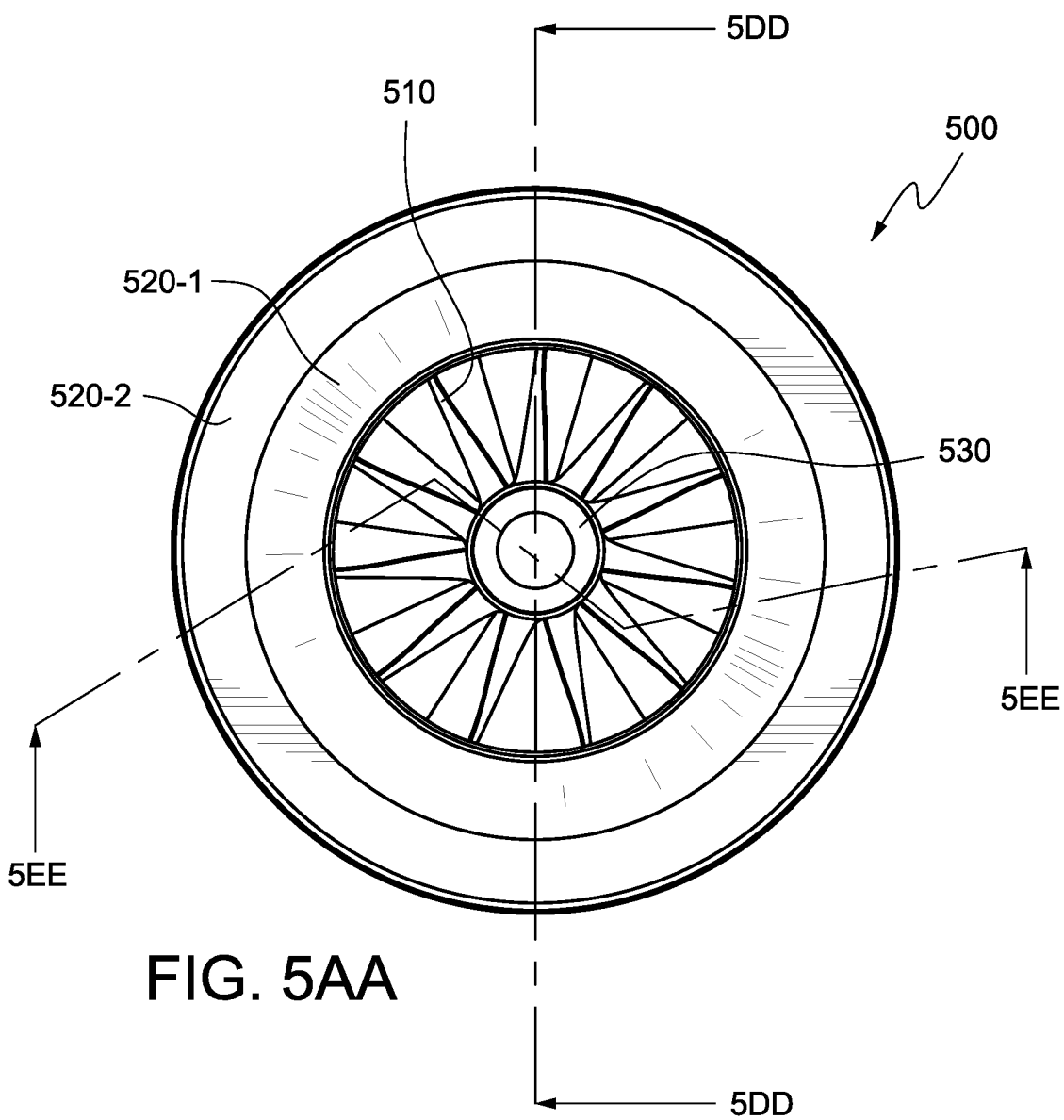
Figure 5B:
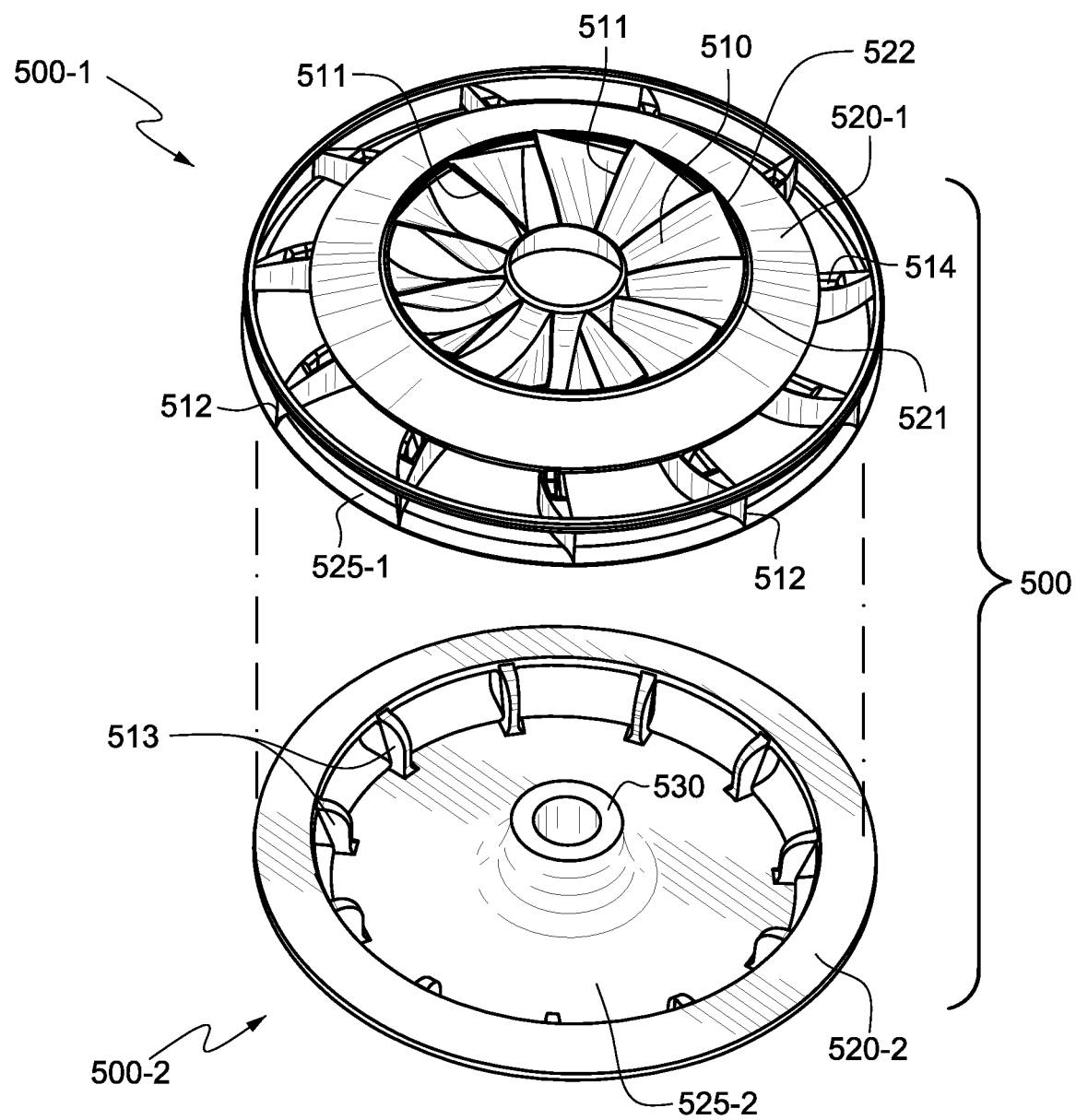
Figure 5C:
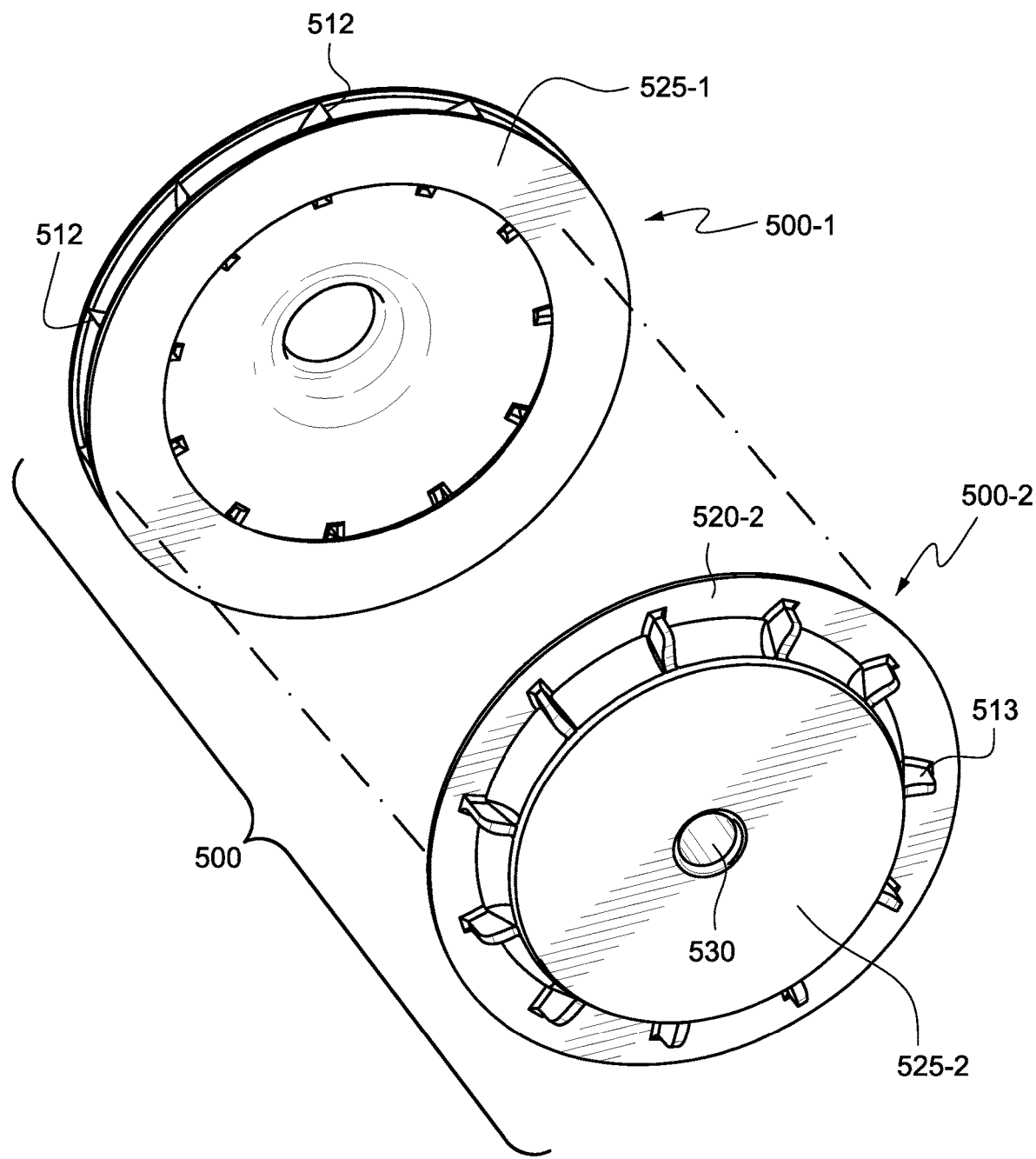
Figure 5D:
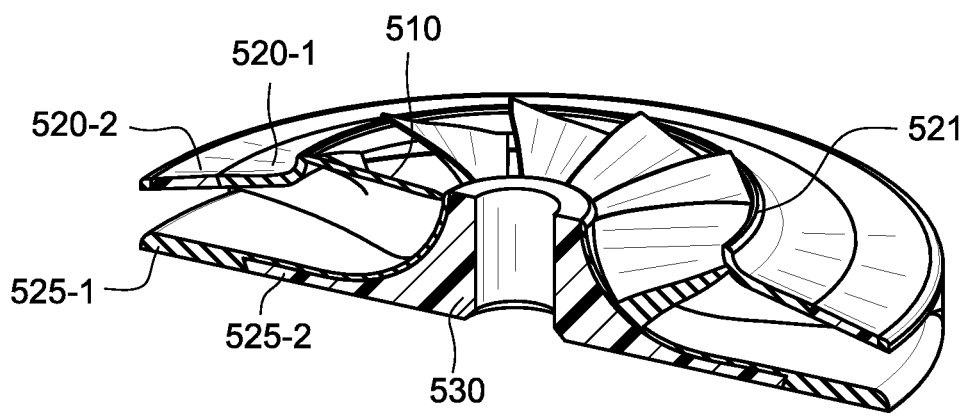
Figure 5E:
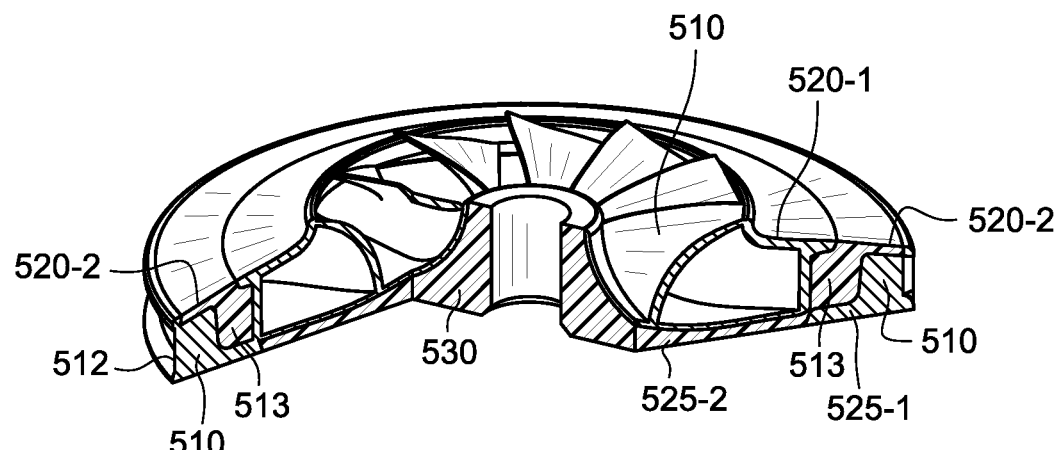
Figure 5F:
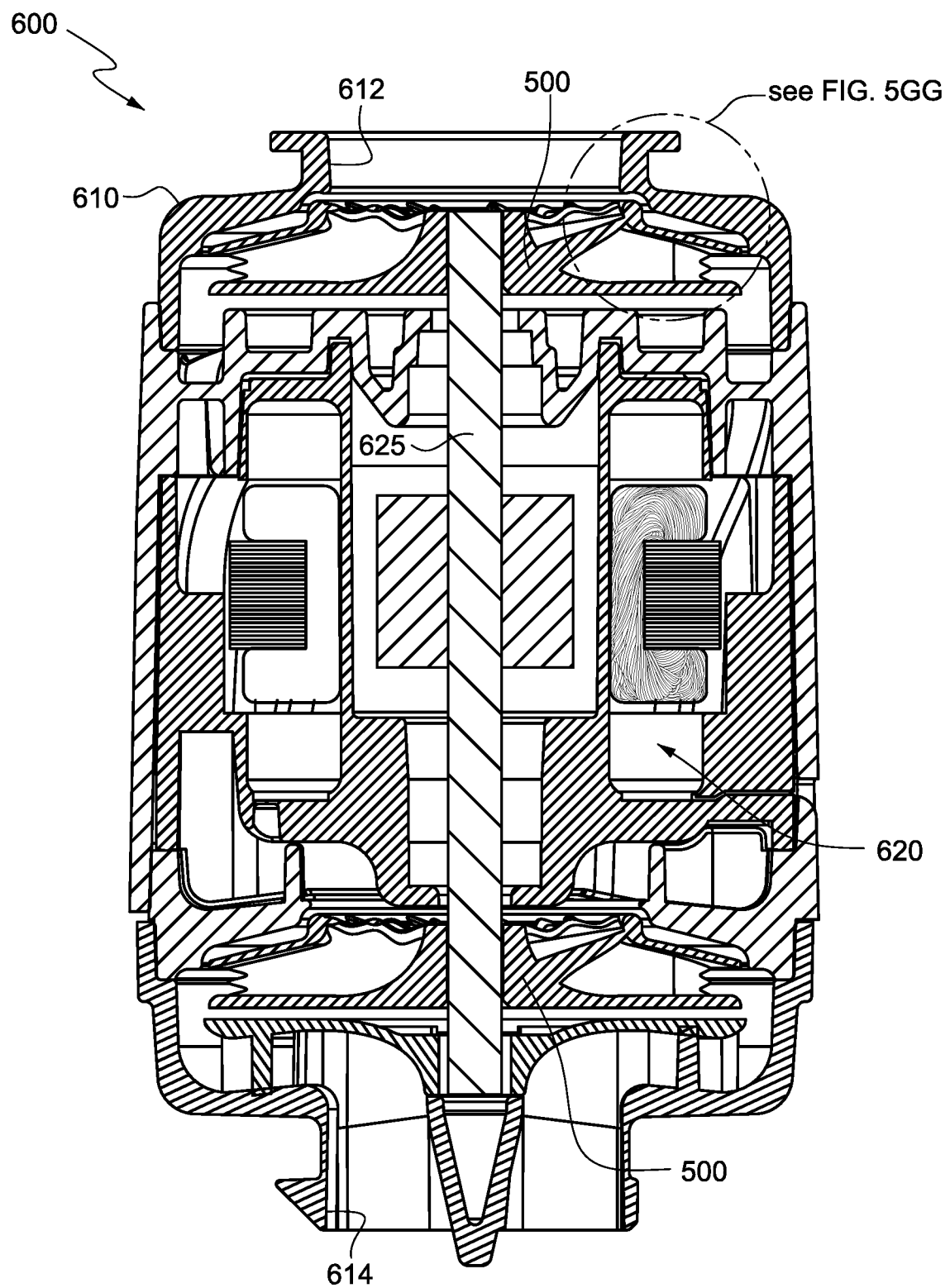
Figure 5G:
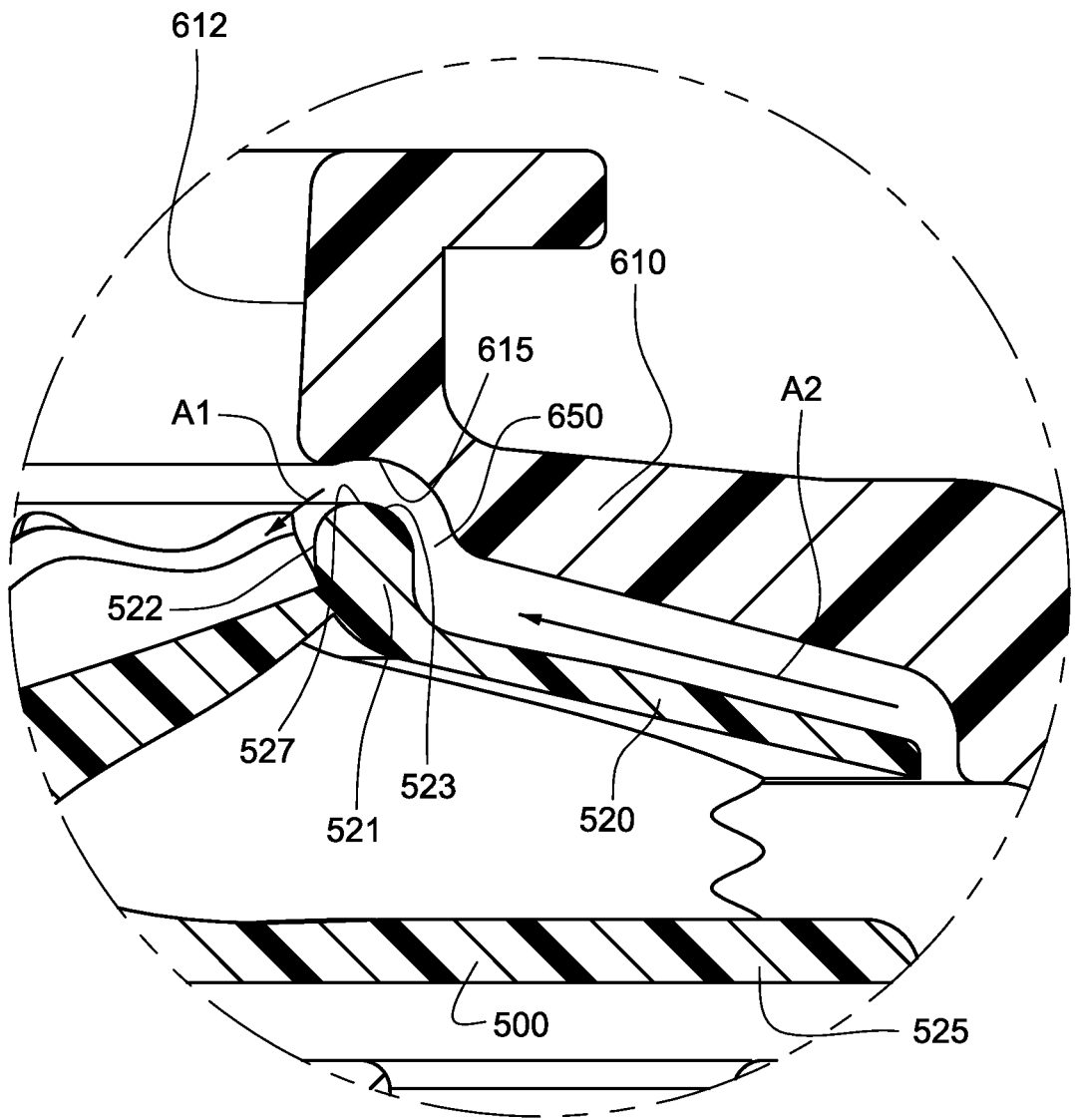
Figure 5H:
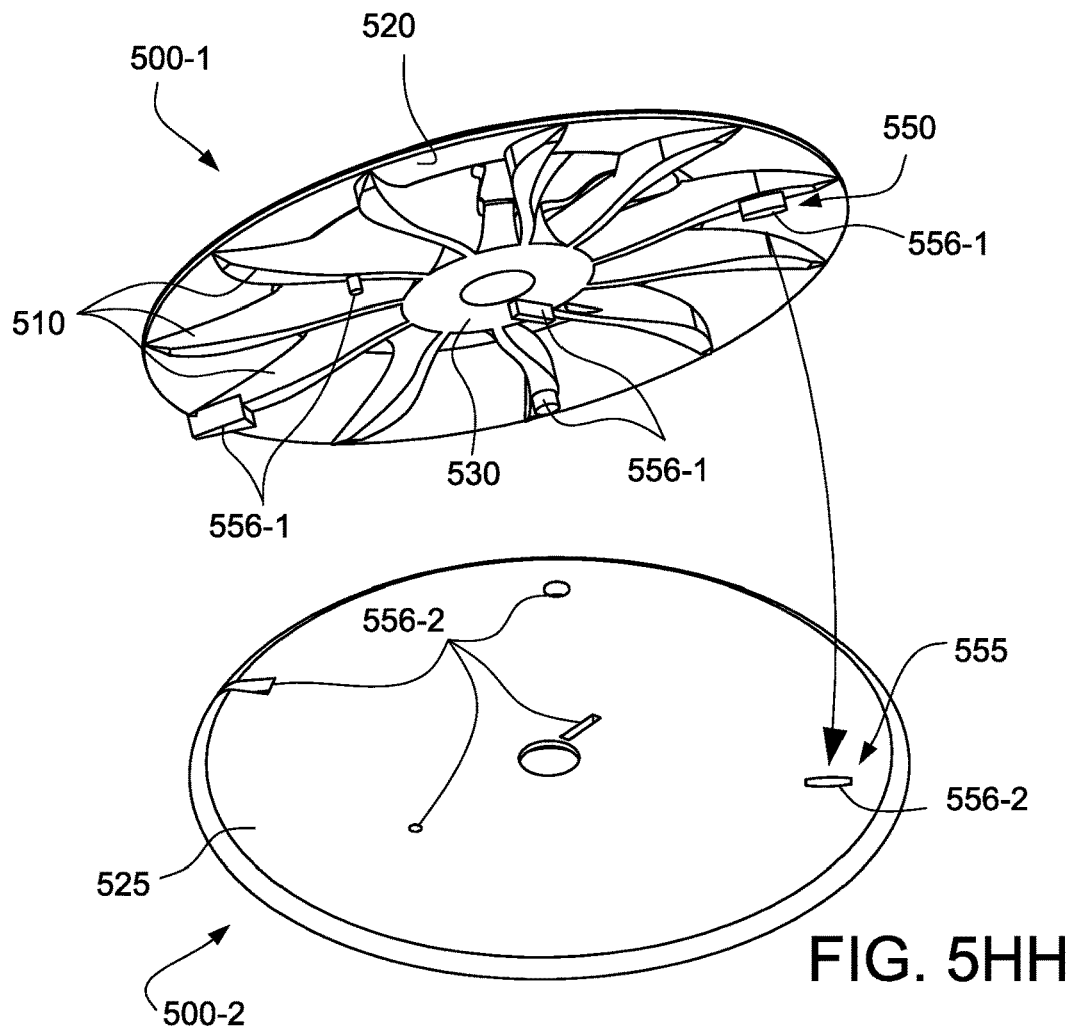
Figure 5I:
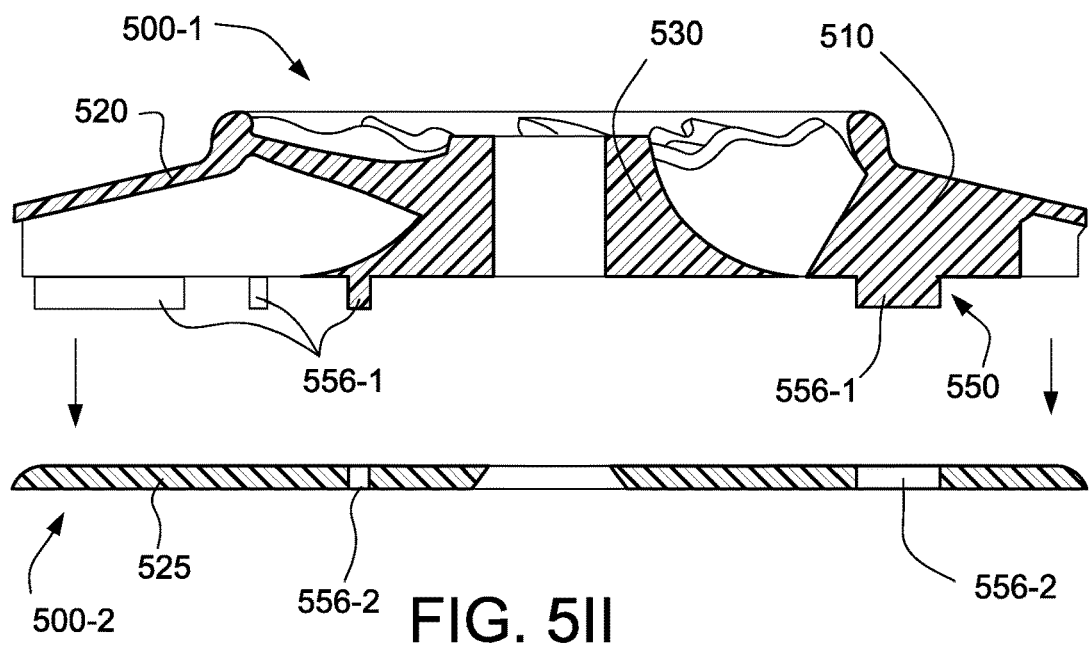
Figure 5J:
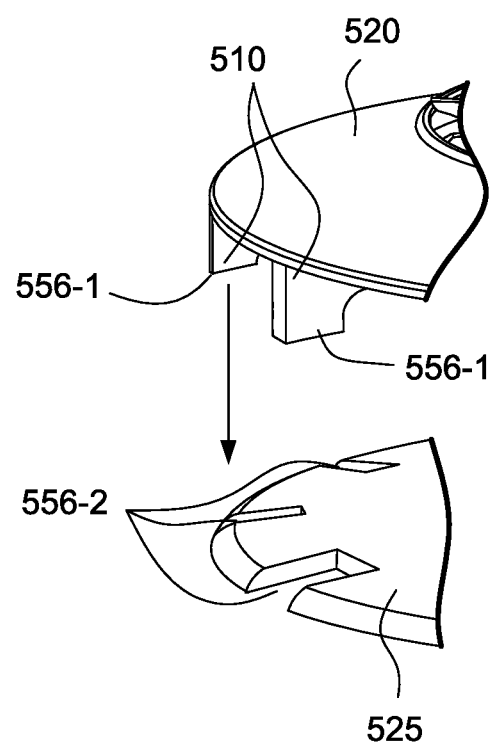
Figure 5K:
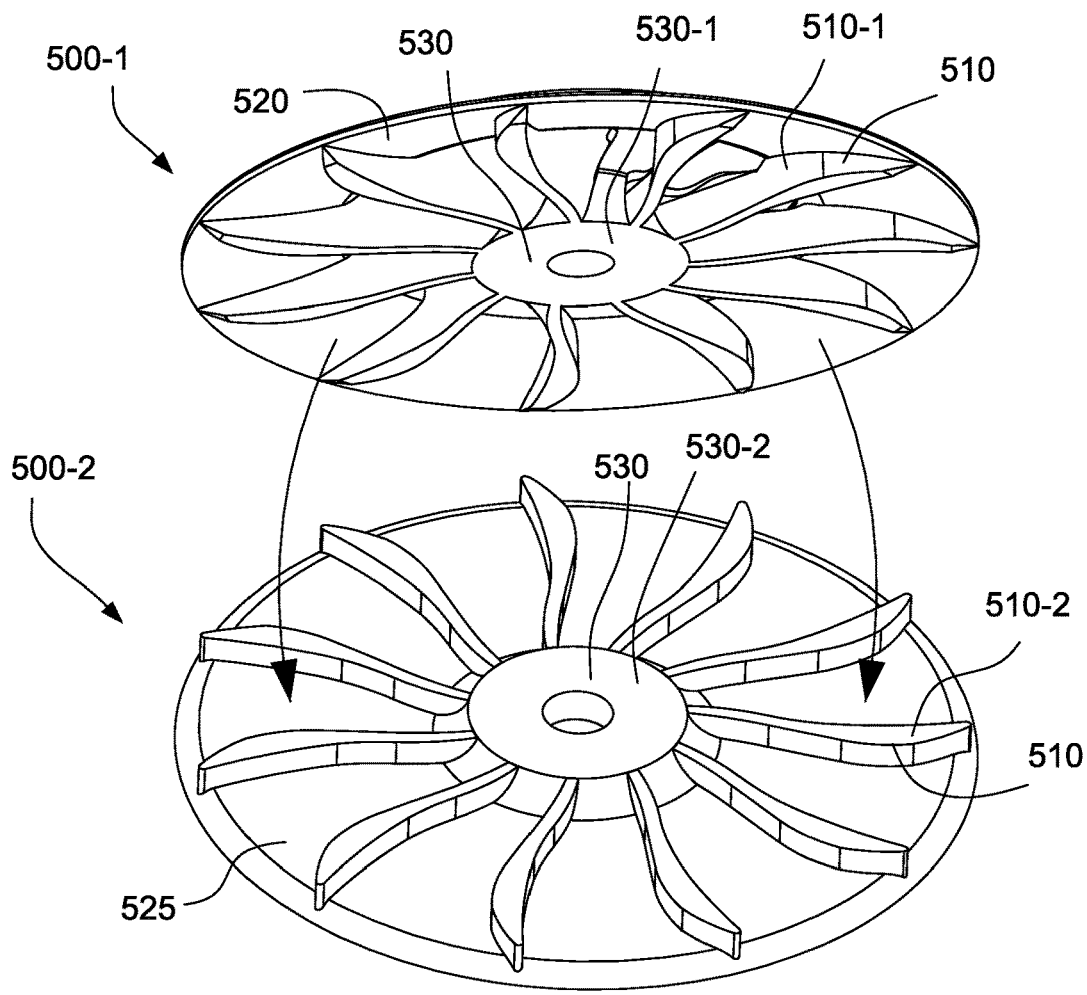
Figure 5L:
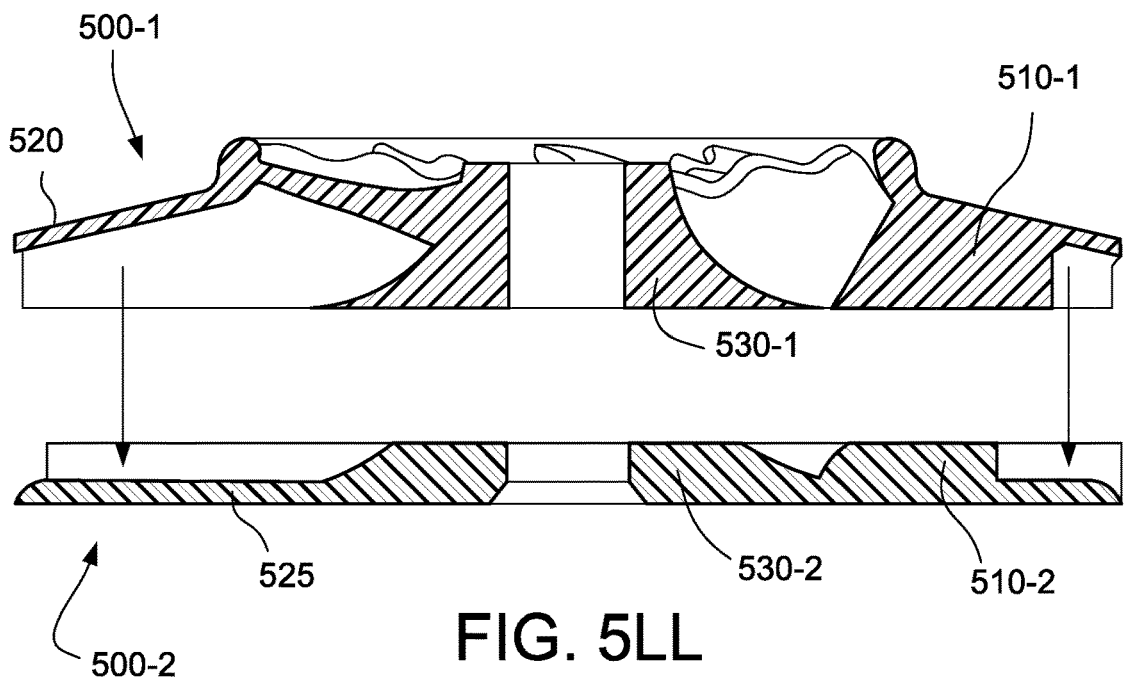
Figure 5M:
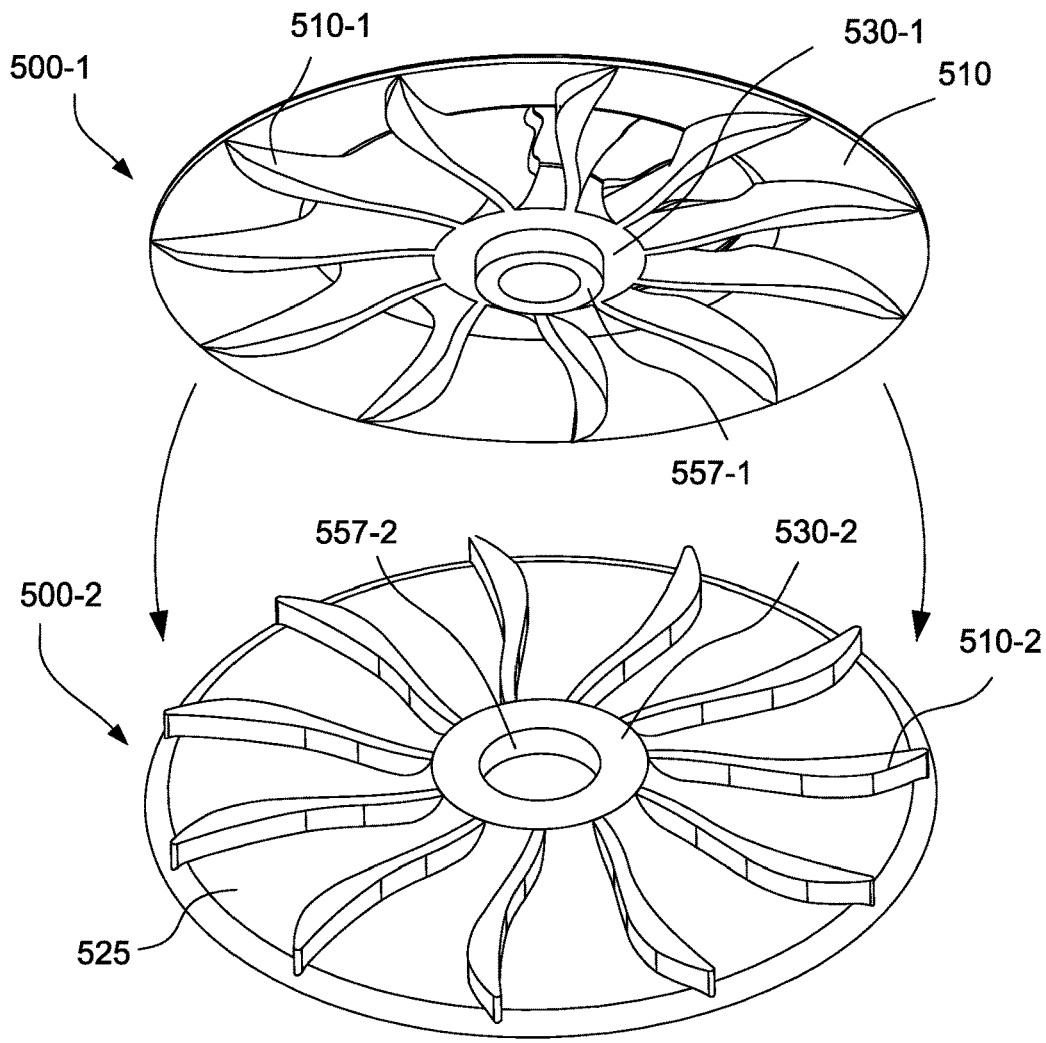
Figure 5N:
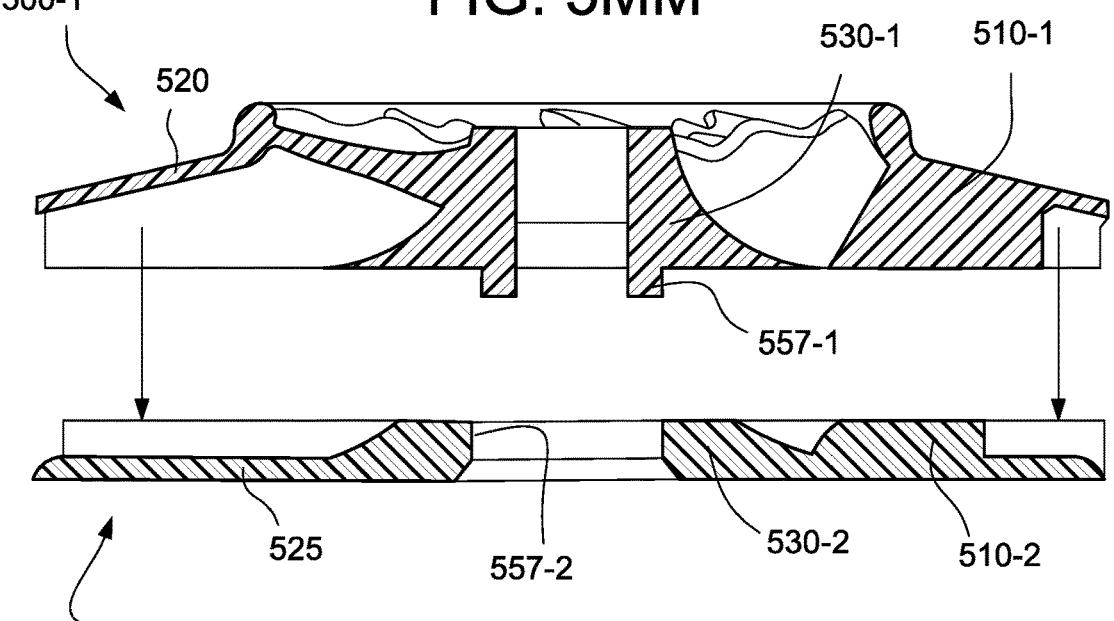
Figure 5O:
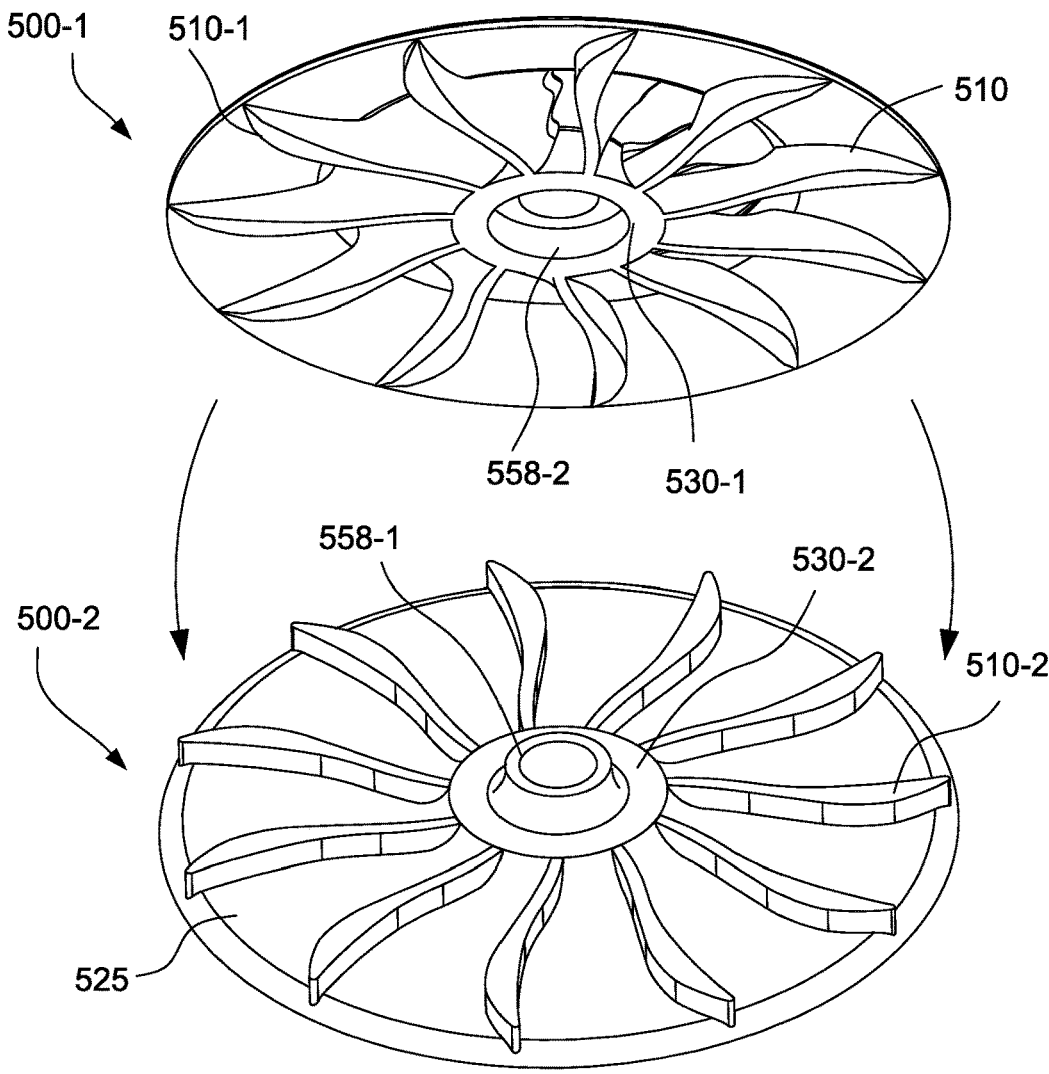
Figure 5P:
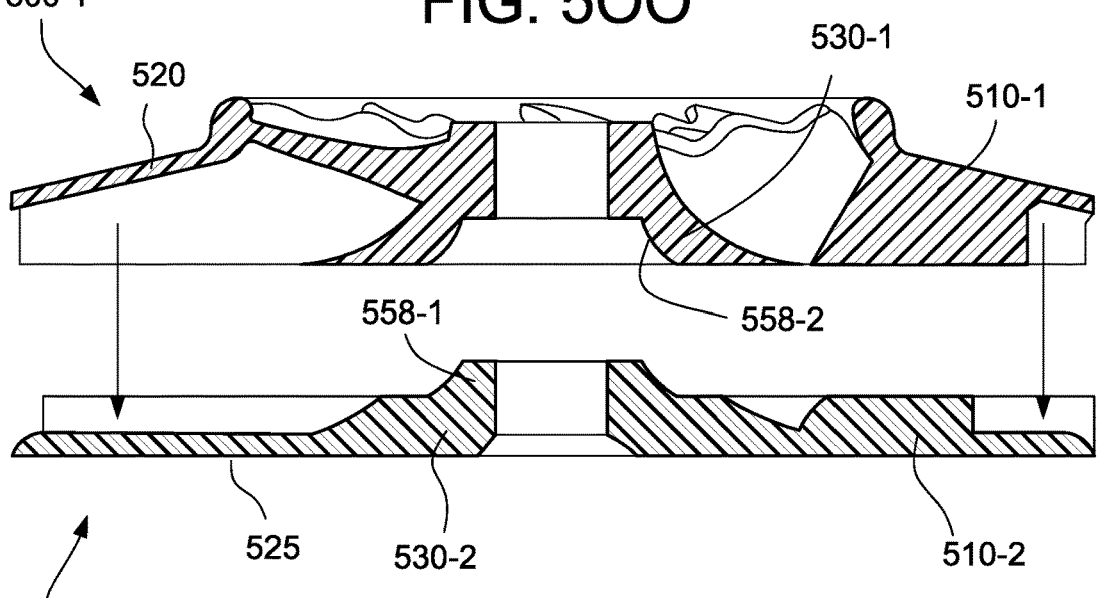
Figure 5Q:
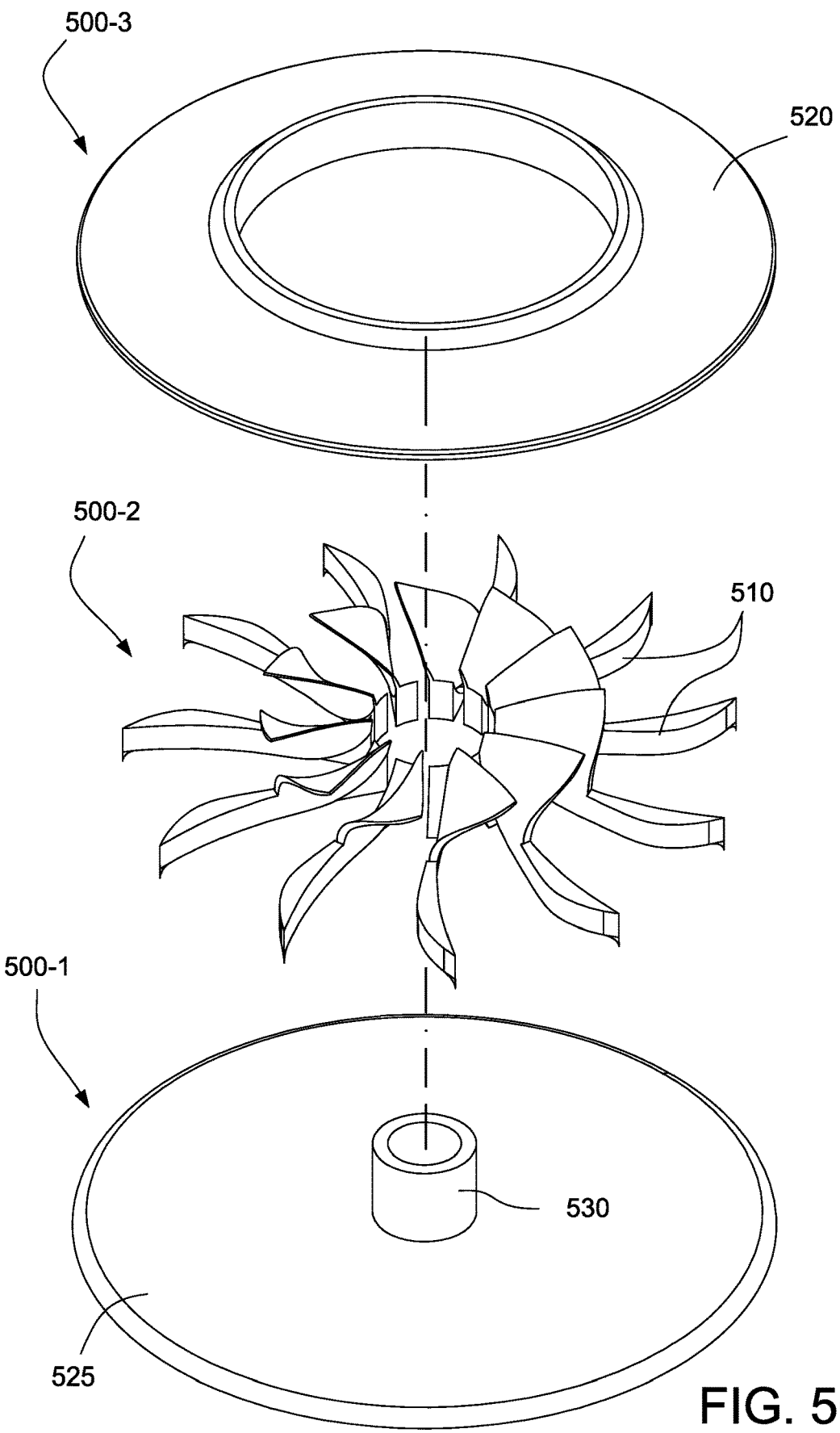
Figure 5R:
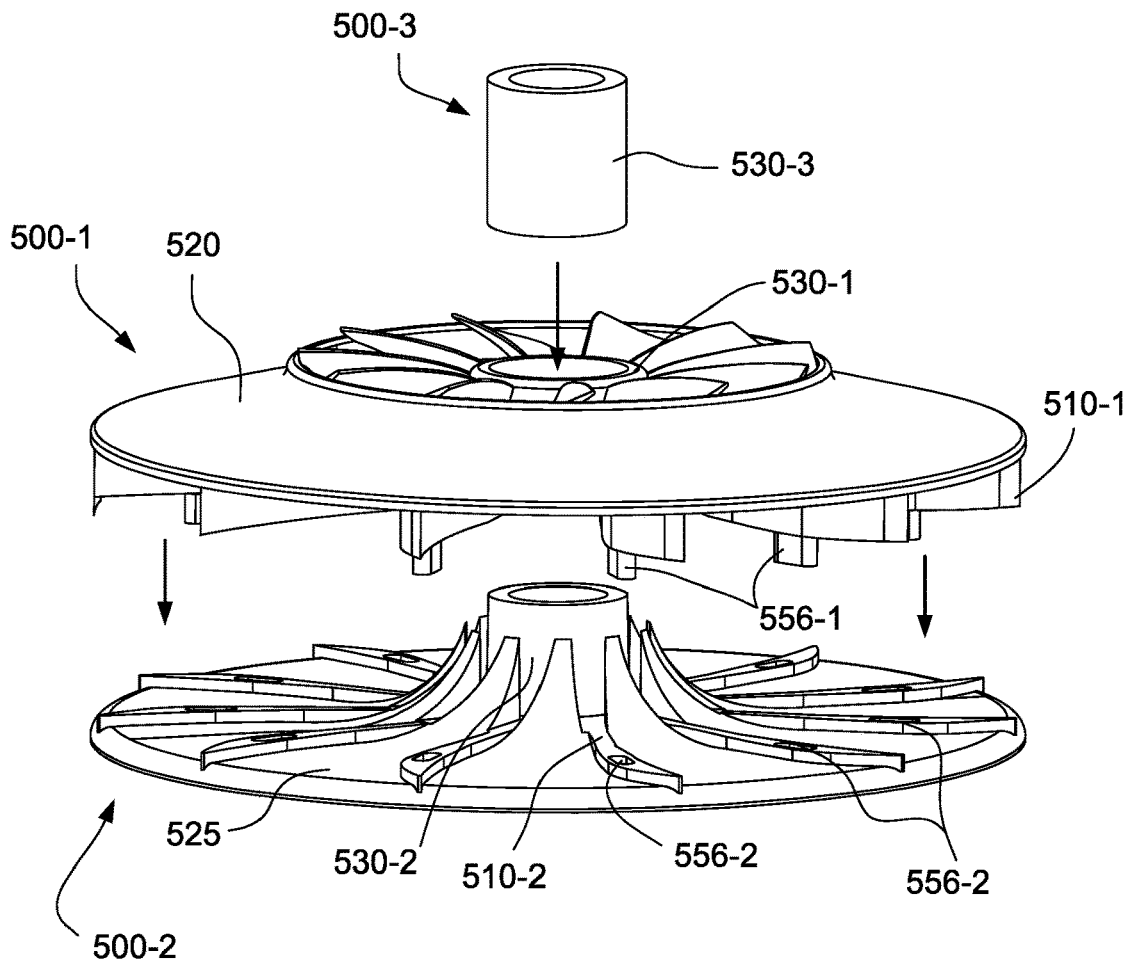
Figure 5S:
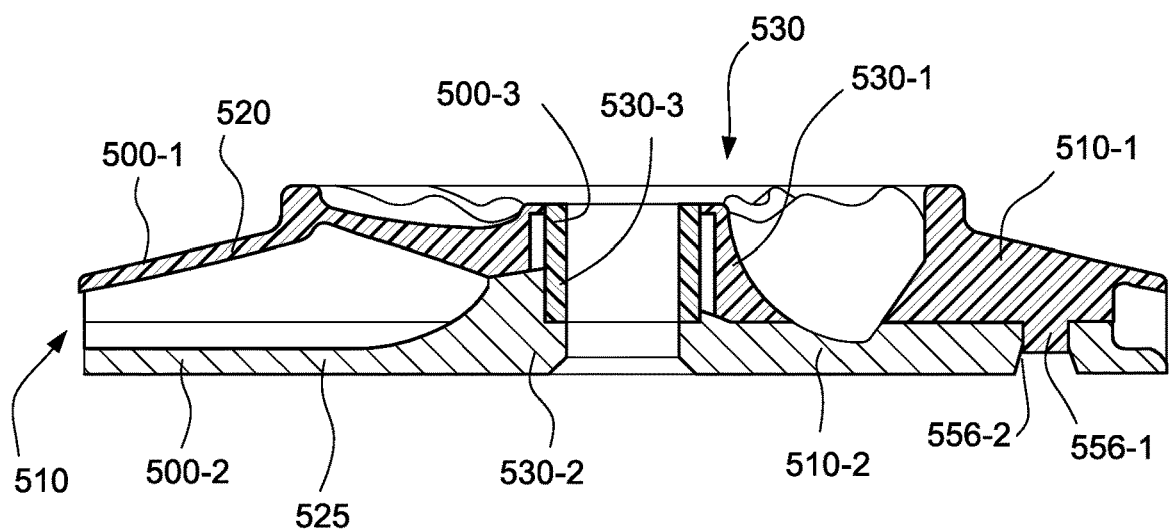
Figure 5T:
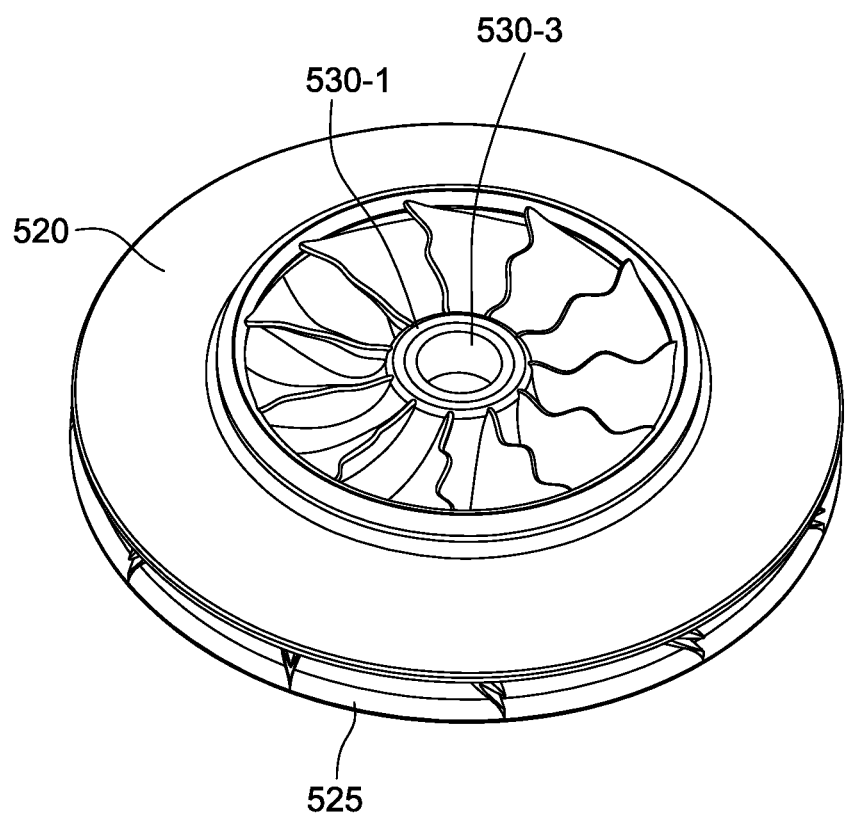

FIG. 5AA shows a plan view of the impeller shown in FIG. 5Y, indicating cross-sections taken for FIGS. 5DD-5EE.

FIG. 5BB shows an exploded view of the impeller shown in FIG. 5Y.

FIG. 5CC shows another exploded view of the impeller shown in FIG. 5Y.

FIGS. 5DD-5EE show cross-sections of the impeller as indicated on FIG. 5AA.

FIG. 5FF shows a cross-section of a blower for an RPT device including impellers in accordance with one form of the present technology.

FIG. 5GG is an enlarged portion of the blower as indicated on FIG. 5FF.

FIG. 5HH shows an exploded view of an impeller in accordance with one form of the present technology.

FIG. 5II shows a cross-section of the impeller shown in FIG. 5HH.

FIG. 5JJ shows a partial exploded view of an impeller in accordance with one form of the present technology.

FIG. 5KK shows an exploded view of an impeller in accordance with one form of the present technology.

FIG. 5LL shows a cross-section of the impeller shown in FIG. 5KK.

FIG. 5MM shows an exploded view of an impeller in accordance with one form of the present technology.

FIG. 5NN shows a cross-section of the impeller shown in FIG. 5MM.

FIG. 5OO shows an exploded view of an impeller in accordance with one form of the present technology.

FIG. 5PP shows a cross-section of the impeller shown in FIG. 5OO.

FIG. 5QQ shows an exploded view of an impeller in accordance with one form of the present technology.

FIG. 5RR shows an exploded view of an impeller in accordance with one form of the present technology.

FIG. 5SS shows a cross-section of the impeller shown in FIG. 5RR.

FIG. 5TT shows is a perspective view of the impeller shown in FIG. 5RR.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

Figure 1A:
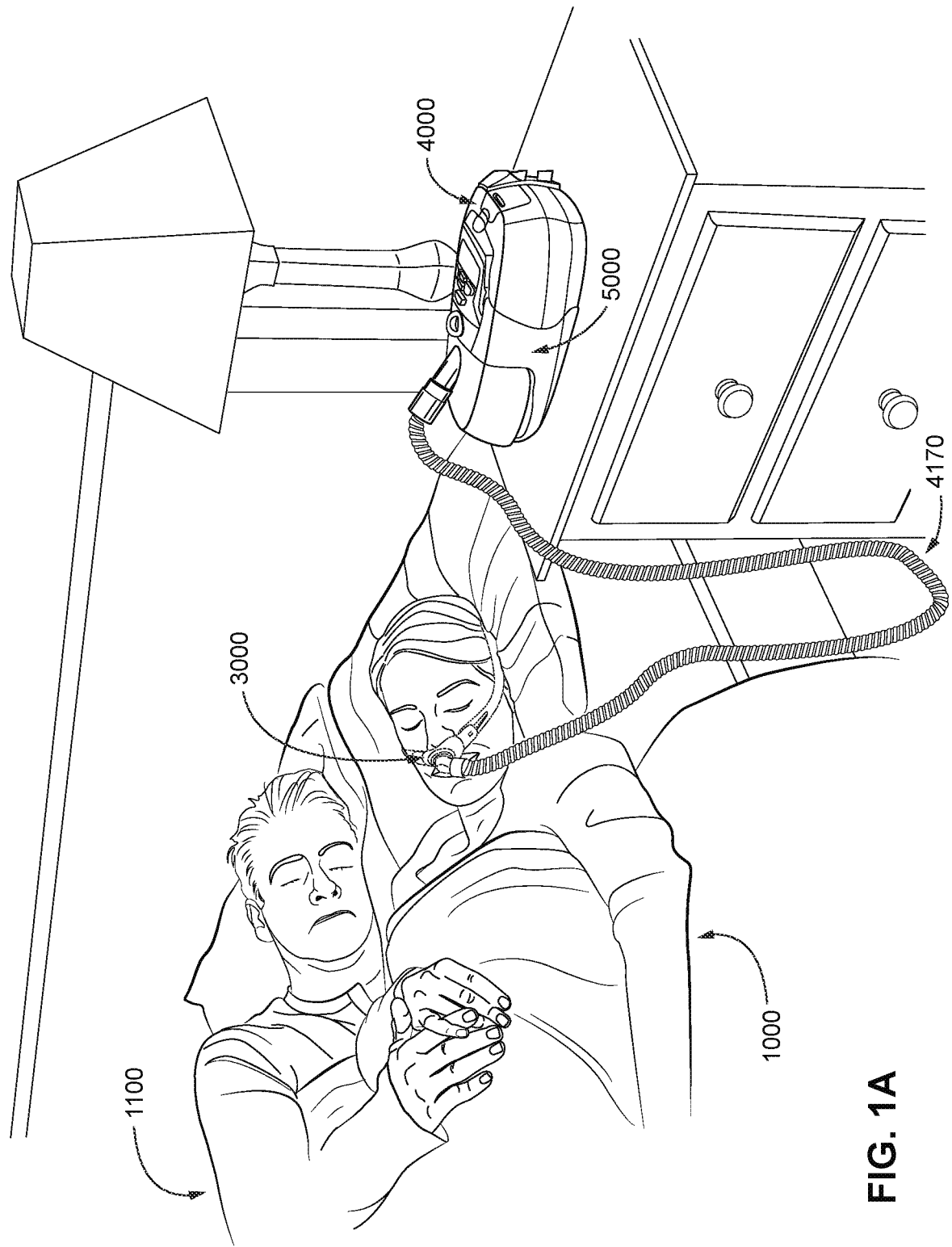
Figure 2A:
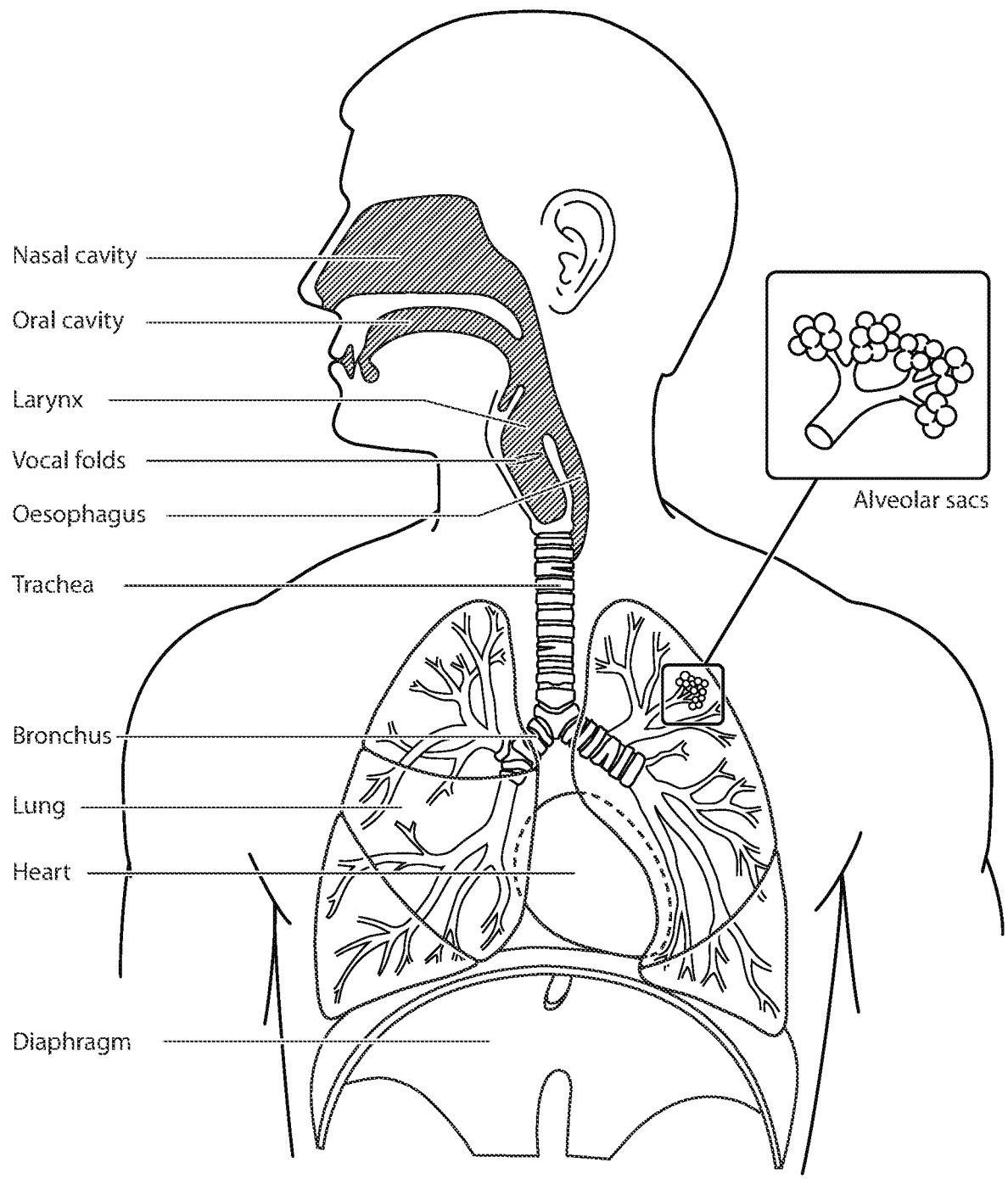
Figure 3A:
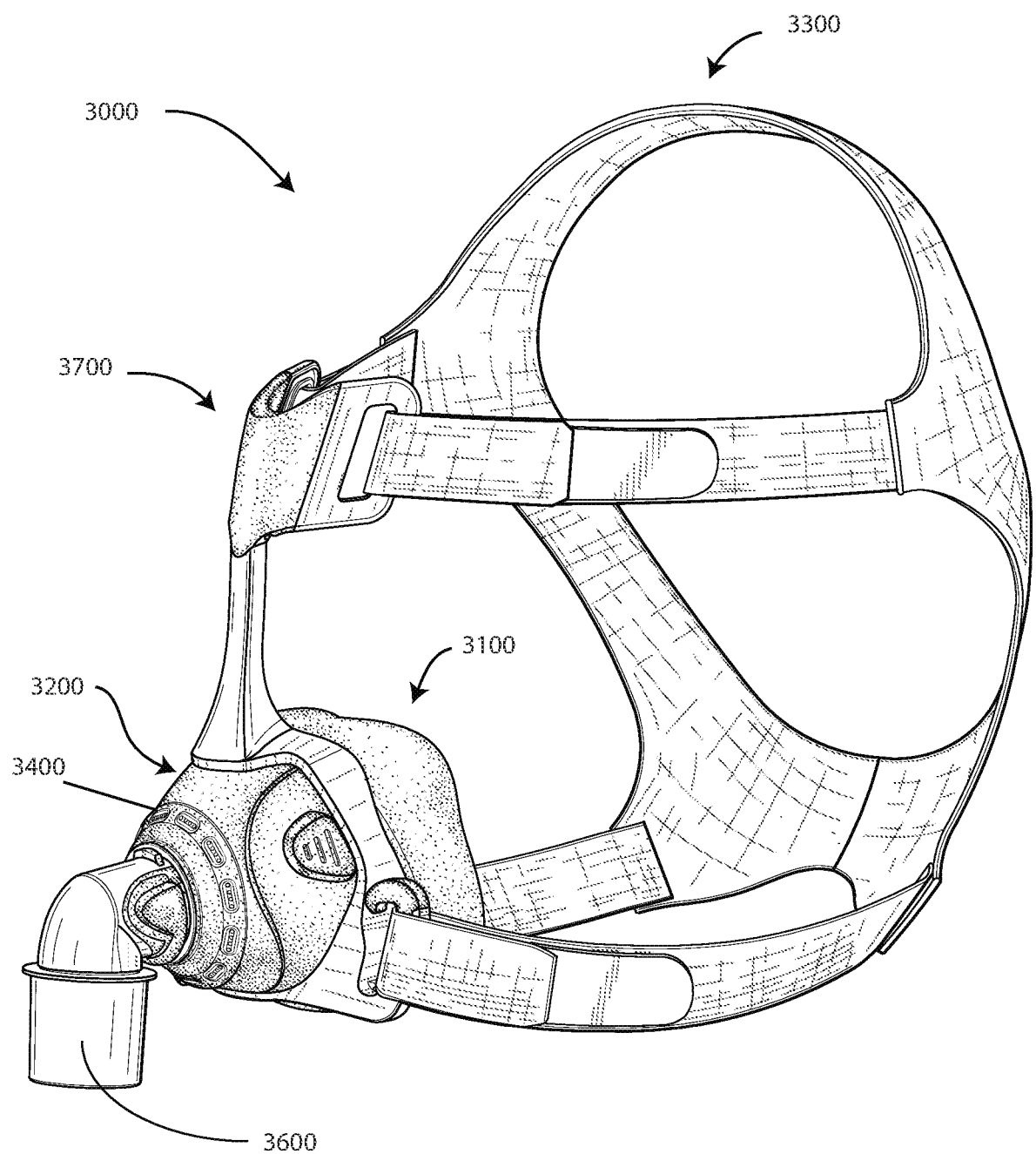

As shown in FIG. 3A, a non-invasive patient interface 3000 in accordance with one aspect of the present technology comprises the following functional aspects: a seal-forming structure 3100, a plenum chamber 3200, a positioning and stabilizing structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.4 RPT DEVICE

An RPT device 4000 in accordance with one aspect of the present technology comprises mechanical, pneumatic, and/or electrical components and is configured to execute one or more algorithms. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 $cm_{2O}$, or at least 10 $cm_{2O}$, or at least 20 $cm_{2O}$.

Figure 4A:
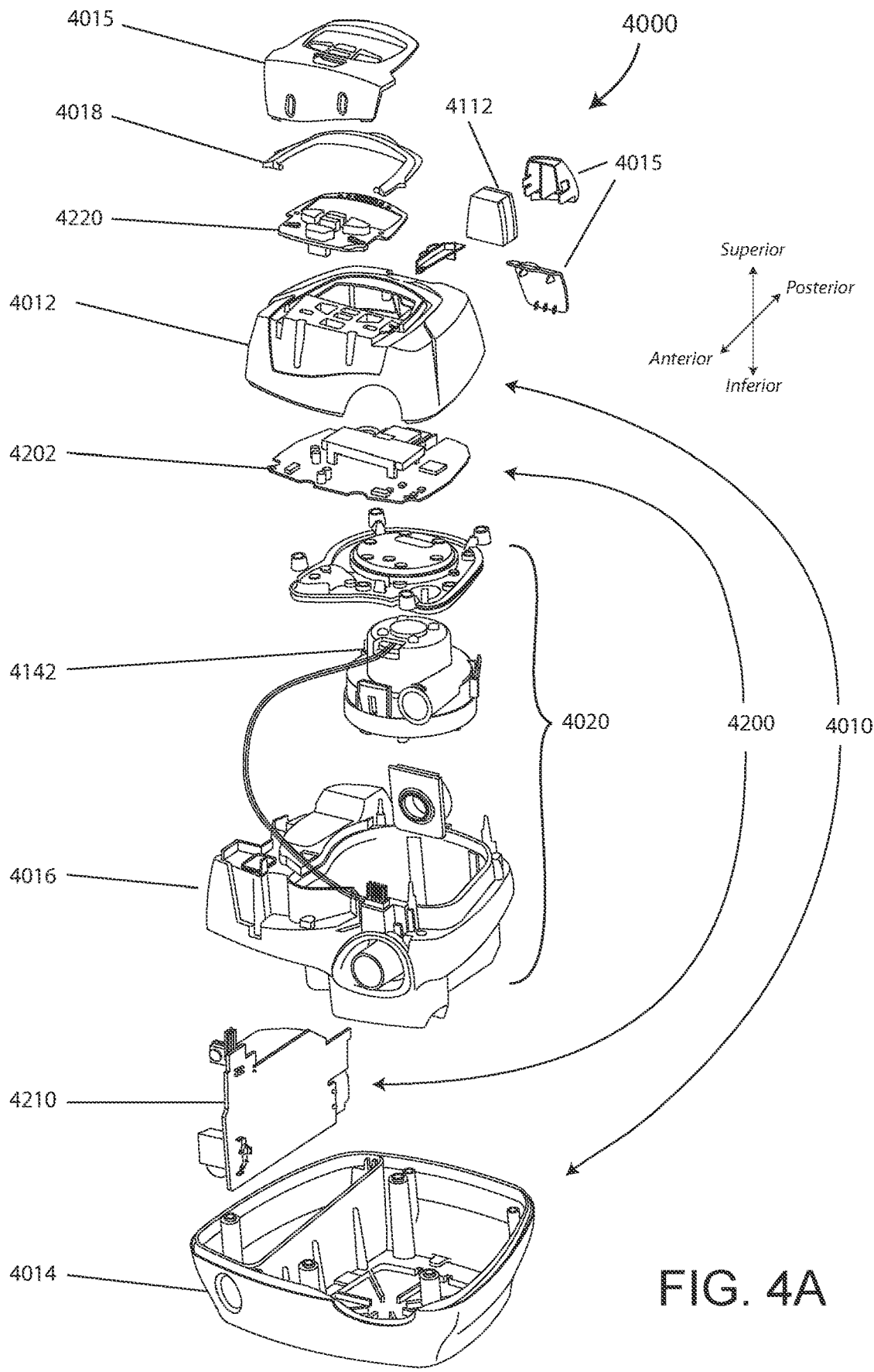

As shown in FIG. 4A, the RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler, a pressure generator capable of supplying air at positive pressure (e.g., a blower 4142), an outlet muffler and one or more transducers, such as pressure sensors and flow rate sensors.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller, a therapy device controller, a pressure generator, one or more protection circuits, memory, transducers, data communication interface and one or more output devices. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Pressure Generator

In one form of the present technology, a pressure generator for producing a flow, or a supply, of air at positive pressure is a controllable blower 4142. For example the blower 4142 may include a brushless DC motor with one or more impellers. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator is under the control of the therapy device controller.

In other forms, a pressure generator may be a piston-driven pump, a pressure regulator connected to a high pressure source (e.g. compressed air reservoir), or a bellows.

5.4.1.1.1 Impeller

Examples of impellers according to the present technology are shown in FIGS. 5A-5TT. The impeller may be suitable for use in a centrifugal blower, such as those described elsewhere in the present specification.

An impeller 500 may comprise one or more of:
- a set of impeller blades 510, each impeller blade 510 comprising a leading edge 511 and a trailing edge 512;
- a first shroud and/or a second shroud, such as a top shroud 520 and/or a bottom shroud 525, at least partly defining a flow passage 540 through the impeller;
- a hub 530 for coupling the impeller to a motor, the hub 530 may be retained by an interference fit to a rotor or motor shaft of the motor for example, however any number of other known retention mechanisms may be suitable.

Where the impeller 500 comprises a first shroud and a second shroud, the first and second shrouds may be arranged such that an axial distance therebetween may generally decrease towards an outer portion of the impeller in the radial direction.

FIGS. 5A to 5N illustrate an impeller 500 according to one example of the present technology. As illustrated, the impeller 500 includes a plurality of impeller blades 510 located between and connected to the first or top shroud 520 and the second or bottom shroud 525. In the illustrated example, the bottom shroud 525 extends to the hub 530 adapted to receive the rotor of the motor.

In the illustrated example, the top shroud 520 is substantially non-planar. For example, the top shroud 520 may taper in the radial direction with respect to the axial direction of the impeller, e.g., the top shroud 520 may comprise a frusto-conical shape. The top shroud 520 includes an outer edge defining a diameter D of the top shroud and an inner edge defining a center opening which provides an impeller inlet 522. An impeller inlet wall 521 extends along the inner edge to define a periphery of the impeller inlet 522. The free end portion of the inlet wall 521 provides a leading edge 523 of the impeller inlet 522. In this arrangement, the top shroud 520 extends to an outer periphery of the impeller, thus the diameter D of the top shroud is the same as the diameter of the impeller. However in other arrangements, the top shroud 520 may not extend to the outer periphery of the impeller, for example only covering a part of the impeller blades.

In the illustrated example, the bottom shroud 525 is substantially planar. As illustrated, the outer edge of the bottom shroud 525 defines a diameter that is substantially similar, e.g., the same, to the diameter D defined by the outer edge of the top shroud 520. In an example, the diameter D of the impeller is less than about 50 mm. The 50 mm dimension is not intended to be strictly limiting and the skilled person would understand that other diameters in the vicinity of 50 mm would give some beneficial effect.

The top and bottom shrouds 520, 525 cooperate to define a flow passage 540 therebetween through the impeller. The flow passage 540 extends from the impeller inlet 522 at an inner portion of the impeller to an impeller outlet 524 at an outer portion of the impeller. The flow passage 540 may include a plurality of channels, each channel defined at least partly by the top and bottom shrouds 520, 525 and impeller blades 510.

In the illustrated example, the flow passage 540 defined between the top and bottom shrouds 520, 525 is structured to narrow (in a normal direction to the direction of the airflow) from the impeller inlet 522 to the impeller outlet 524, i.e., the spacing or distance between the top and bottom shrouds 520, 525 lessens or tapers from the impeller inlet to the impeller outlet.

That is, the top and bottom shrouds 520, 525 are configured such that the flow passage is narrower in the axial direction at the outer portion of the impeller than at the inner portion of the impeller, i.e., an axial distance between the top and bottom shrouds 520, 525 may generally decrease towards the outer portion of the impeller in the radial direction. For example, FIG. 5B shows exemplary axial distances d1 and d2 between the top and bottom shrouds 520, 525, with d1 along an inner portion of the impeller larger than d2 along an outer portion of the impeller and the axial distance gradually decreasing from d1 to d2 in the radial direction. Additionally, the top and bottom shrouds 520, 525 are configured such that the axial distance between them at the outlet of the impeller (i.e., d2) is smaller than the radial dimension of the inlet.

Thus, an impeller according to an aspect of the present technology may comprise a flow passage 540 comprising a plurality of channels, each channel configured with a decreasing height along a direction of the air flow therethrough.

5.4.1.1.1.1 Impeller inlet

An impeller according to the present technology may comprise a relatively large impeller inlet size as a proportion of the impeller diameter D. In one form, the impeller inlet 522 may be defined by a periphery of the top shroud 520, such as in FIG. 5B, where the inlet wall 521 of the top shroud 520 is shown in the cross section.

In general, it may be a disadvantage to increase a size of the impeller inlet in a centrifugal blower while maintaining other dimensions (e.g., impeller diameter), as such an increase may decrease an effective diameter of the impeller in which pressure using the centrifugal effect may be imparted to the air flowing through the blower. In other words, enlargement of an impeller inlet may result in a configuration wherein insufficient pressure is generated by the blower.

However, for an application such as in RPT devices, where a small size of the device is desirable for aesthetic reasons, convenient bedside placement of the RPT device and portability, a designer may wish to reduce a size of the impeller. However, as an impeller diameter is reduced, a velocity of the air flow through the impeller is increased, adversely affecting noise and efficiency of the impeller, for example caused by changes to an aerodynamic behaviour due to the increase in air velocity.

As described elsewhere, an RPT device may be relatively unique in that it is preferably small and quiet for bedside/nocturnal/sleep-time use, while requiring generation of sufficient pressures and flow rates for respiratory therapy. For use in small, possibly portable, RPT devices, it was found that a decrease in impeller diameter may be accompanied by a relative increase in the impeller inlet diameter.

In one form, the impeller of a diameter D of less than 50 mm may comprise an impeller inlet 522, wherein a diameter (dinlet as shown in FIG. 5A) of the impeller inlet 522 is at least 50% of the diameter D of the impeller. The 50% proportion is not intended to be strictly limiting and the skilled person would understand that other proportions in the vicinity of 50% would give some beneficial effect. In one example, the impeller may comprise a diameter D of 40 mm with an impeller inlet diameter &lei of 20 mm, 22 mm or 24 mm.

According to another aspect of the present technology, the impeller inlet wall 521, or a periphery of the impeller inlet 522, may comprise a relatively large radius to improve overall impeller and/or blower performance. An increased radius at a portion facing the incoming air flow into the impeller may advantageously lead to improved efficiency, as the air flow remains attached to the inlet wall 521.

In one form, a leading edge of the periphery of the impeller inlet 522, e.g., the leading edge 523 at the free end portion of the inlet wall 521 of the top shroud 520 (as best shown in FIG. 5B), comprises a cross sectional shape with a radius of at least 0.5 mm. In another form, a radius of the leading edge of the first or top shroud 520 is greater than 70% of the maximum thickness of the body of the first shroud 520, such as greater than 85%, 100% or 115%. In another form, a radius of the leading edge 523 of the first or top shroud 520 is greater than the maximum thickness of a body of the first shroud 520. In another form, a leading edge of the first or top shroud 520 comprises a cross sectional shape with a radius of at least 1% of the diameter D of the impeller. In use, an air flow entering the impeller at the impeller inlet 522 is discouraged from detachment at or around the radius, e.g., to reduce noise and improve efficiency.

5.4.1.1.1.2 Impeller Blades

The impeller 500 may comprise a plurality of impeller blades 510. In the illustrated example, the impeller includes 11 blades 510. However, it should be appreciated that the impeller may include other suitable numbers of blades, e.g., 3 or more blades, e.g., 5-20 blades, e.g., 7 blades, 11 blades, 13 blades.

Each impeller blade 510 extends from the hub 530 towards the outer edge of the impeller. Each impeller blade may be connected to the top and bottom shrouds 520, 525. Each impeller blade comprises a leading edge 511 and a trailing edge 512. It should be noted that the terms 'leading edge' and 'trailing edge' are to be understood akin to its usage in aeronautics, referring to a portions of a wing, rather than a narrow geometric sense of an 'edge'.

For example, a 'leading edge' may refer to a part of the impeller blade that generally first contacts the air coming into the impeller. Similarly, a 'trailing edge' may refer to a part of the impeller blade that generally last contacts the air as it leaves the impeller.

In the illustrated example, the impeller blades 510 are sandwiched between the top and bottom shrouds 520, 525. As illustrated, each blade 510 is overlapped by the top shroud 520 such that a first edge 515 along an outer portion of the blade is in contact with the top shroud 520 and the leading edge 511 along an inner portion of the blade is exposed through the impeller inlet 522, i.e., leading edge 511 extends between the inlet wall 521 and the hub 530 defining the inlet 522 into the impeller. Each blade 510 is overlapped by the bottom shroud 525 such that a second edge 517 is in contact with the bottom shroud 525 and hub 530 along its entire length. The trailing edge 512 is exposed through the impeller outlet 524 between the outer ends of the top and bottom shrouds 520, 525.

In the illustrated example, each blade 510 extends to the outer edges of the top and bottom shrouds 520, 525, e.g., the blades 510 do not extend beyond the top and bottom shrouds 520, 525. In alternative examples, the blades 510 may extend beyond or extend short of the outer edges of the top and bottom shrouds 520, 525.

According to one aspect of the present technology, the leading edge 511 and/or the trailing edge 512 of an impeller blade 510 may be very thin, such that turbulence and noise is reduced at the inlet and outlet of the impeller. In an example, the thickness of the leading edge 511 and/or the trailing edge 512 of an impeller blade 510 may be less than about 0.2 mm, e.g., less than about 0.1 mm, such as measured at its thinnest portion, or measured at its outermost portion (i.e., most downstream portion). The 0.2 mm is not intended to be strictly limiting and the skilled person would understand that other thicknesses the vicinity of 0.2 mm would give some positive effect. Furthermore, uniquely to RPT devices, some impeller designs may be such that a seemingly small reduction in a size of the leading (and/or trailing) edge may have a positive effect on the air flow of the impeller and efficiency of the RPT device.

In an example, the cross-sectional thickness of each blade 510 may be variable or tapered, e.g., along at least a portion of its length in plan view. For example, as shown in FIGS. 5K-5N, an outer portion of each blade 510 may include a cross-sectional thickness that tapers towards the trailing edge 512.

Also, as shown in FIGS. 5K-5N, each blade 510 may be curved and/or provide curved exterior surfaces, e.g., along at least a portion of its length in plan view. For example, as shown in FIGS. 5K-5N, an outer portion of each blade 510 may provide curved surfaces 519 along its length towards the trailing edge 512, e.g., to provide a smooth air flow passage to reduce turbulence and hence noise.

Further, as shown in FIGS. 5K-5N, the flow passage defined between adjacent blades 510 is structured to enlarge, e.g., along at least a portion of its length in plan view. For example, as shown in FIGS. 5K-5N, the flow passage defined between adjacent blades 510 is structured to enlarge towards the trailing edges 512, e.g., to increase pressure.

An impeller blade 510 may be inclined, as shown in FIGS. 5C, 5P or the cross sections shown in FIGS. 5K-5N. For example, the leading edge 511 of each blade 510 may be inclined, e.g., by an angle greater than 45 degrees, with respect to an axis of the hub 530 or motor.

In the example of FIGS. 5A-5N, the trailing edge 512 extends substantially parallel to an axis of the hub 530.

In some forms, as shown in FIGS. 5O-5S, the impeller blade 510 may comprise one or more serrations, e.g., the leading edge 511 and/or the trailing edge 512 may comprise one or more serrations arranged along the leading edge 511 and/or the trailing edge 512. Some examples of potentially suitable arrangements of leading edge and/or trailing edge serrations may be found on PCT Patent Application Publication No. WO 2016/201516, the contents of which is incorporated herein by reference in its entirety.

5.4.1.1.1.3 Impeller Construction

Many prior art impellers, particularly in the field of respiratory pressure therapy devices, have been manufactured by injection moulding a polymer material. Typical reasons may have included (but not limited to):
- low cost per part, particularly as volume produced increases;
- smooth surface finish from injection moulding, which may minimize any turbulence generated;
- high reproducibility of moulded parts, ensuring consistency and quality control; and
- low density (and relatively high stiffness and strength) of plastic used, helping to minimize mass and rotational inertia, such that rapid acceleration and deceleration may be more easily achievable.

As a consequence of using injection moulding, particular impeller geometries may have been either extremely difficult to achieve, or simply not possible using injection moulding only. For example, an impeller employing curved and swept blades, as well as top and bottom shrouds, may be extremely difficult to manufacture using an injection moulding process. That is, once the component had been moulded, it could not be extracted from the moulding tool, as the tool and the component would now be intertwined.

In another example, an injection moulded plastic component may require a minimum wall thickness, such that the molten plastic being injected may be able to flow sufficiently within the mould without requiring excessive pressures.

In some examples, an impeller comprising one or more of the aspects described herein may be manufactured by employing alternative manufacturing methods or constructions, while overcoming some of the disadvantages previously associated with such methods.

Additive Manufacturing

In one aspect, an impeller according to the present technology may be produced by an additive technique, sometimes referred to as "three-dimensional (3D) printing", potentially using a metallic material such as titanium, aluminium or stainless steel.

In many applications, even in some instances of RPT devices, a metallic impeller may have a disadvantage over a polymer impeller due to the increased rotational inertia. As alluded to earlier, a higher rotational inertia of an impeller may require an increased capability from a motor driving the impeller, as the requisite torque to accelerate or decelerate the impeller is increased. In turn, the motor may increase in size, and requirements for the power supply and/or a battery may accordingly be increased.

However, for a relatively small impeller, some of these problems may be ameliorated, whereby use of a metallic material becomes more feasible. As a diameter of the impeller decreases, the corresponding rotational inertia decreases as the square of the radius: $I \propto mr^2$, where I refers to rotational inertia, m to mass of the impeller and r is the radius of the impeller. This is effectively a power of 4 dependency of rotational inertia on radius, since for a given material and thickness the mass of the impeller also varies as the square of the radius.

Thus, advantageously, it was found that for the present application and size, additive manufacturing techniques using a metallic material may be particularly suitable such that high-efficiency geometry such as those described herein may be achieved.

In some instances, a material (e.g., metallic material) with the same/similar coefficient of expansion as a rotor (e.g., motor shaft) may be chosen (e.g., the shaft and the impeller may comprise the same metal or metallic material), such that if the impeller is press fit onto the rotor, any thermal expansion would occur uniformly between the two joined, rotating components. This may help to preserve integrity of an interference fit despite variations in temperature, which may vary more within a motor than for example in ambient air.

Multi-Part Construction

According to one aspect of the present technology, such as shown in FIGS. 5T-5TT, an impeller 500 may comprise multiple portions.

In some forms, one portion may comprise a different material to another portion. For instance, a first portion may comprise a deformable, resilient material and a second portion may comprise a rigid material. In an example, the rigid material may be a plastic material, and the resilient material may be an elastomeric material such as a silicone material.

In the example shown in FIGS. 5Y-5EE, a first moulded part or portion, i.e., a first impeller portion 500-1, may be structured and arranged to be coupled to a second moulded part or portion, i.e., second impeller portion 500-2, to produce the impeller 500. The first impeller portion 500-1 may comprise a deformable, resilient material (e.g., an elastomeric material such as silicone) that may be coupled with the second impeller portion 500-2 comprising a rigid material (e.g., rigid plastic). For example, a manufacturing process may first produce (e.g., mould) the second impeller portion 500-2, onto which the first impeller portion 500-1 may be overmoulded. Other forms of coupling, such as chemical bonding or mechanical bonding, may be suitable that are not overmoulded.

As illustrated, the first impeller portion 500-1 comprises the plurality of impeller blades 510, a portion of the top shroud 520 (i.e., an inner or first portion 520-1 of the top shroud which comprises the inlet wall 521 defining the periphery of the impeller inlet 522), and a portion of the bottom shroud 525 (i.e., an outer or first portion 525-1 of the bottom shroud). The second impeller portion 500-2 comprises a portion of the top shroud 520 (i.e., an outer or second portion 520-2 of the top shroud), the hub 530 structured for coupling to the rotor, a portion of the bottom shroud 525 (i.e., an inner or second portion 525-2 of the bottom shroud), and inner blade portions 513. The inner blade portions 513 are adapted to be received in corresponding openings 514 provided within the impeller blades 510, e.g., to add rigidity to the impeller blades 510.

When the first impeller portion 500-1 is overmoulded to the second impeller portion 500-2 to produce the impeller 500, the inner portion 520-1 and the outer portion 520-2 cooperate to form the top shroud 520, the outer portion 525-1 and the inner portion 525-2 cooperate to form the bottom shroud 525, and the inner blade portions 513 add interior rigidity to the impeller blades 510, i.e., inner blade portions 513 add a rigid material to the impeller blades 510. In such arrangement, the impeller blades 510 and the leading and trailing edges 511, 512 thereof comprise an elastomer material (e.g., silicone), and the hub 530 comprises a rigid material for coupling to the rotor.

By such a construction, an impeller may be produced with the desired, advantageous aerodynamic features described herein, which can be injection moulded. That is, using such a construction, the manufacturer may be able to withdraw a 'core' of the injecting moulding tool, as the first impeller portion 500-1 (e.g., comprising silicone) would be able to resiliently deform to allow removal of the injection moulding tool. Further advantageously, such a material (e.g., silicone) of the first impeller portion 500-1 may allow manufacture of thinner wall sections than plastic, thus enabling manufacture for example of the thin impeller blade leading edge 511 and/or trailing edge 512 described above.

Also, a strategic use of such a deformable, resilient material, rather than construction of an impeller entirely from a deformable, resilient material, may help to manufacture an impeller wherein an overall structural integrity is sufficient for durability as well as limiting deformation in operation.

In other forms, an impeller may comprise multiple portions, each not necessarily comprising different materials to each other.

In the example shown in FIGS. 5T-5X, the first impeller portion 500-1 and the second impeller portion 500-2 may be separately moulded and assembled or fastened together. In an example, the first and second portions may each comprise a rigid material (e.g., rigid plastic, such as PEEK, also known as polyetheretherketone). In another example, the first portion may comprise a deformable, resilient material (e.g., an elastomeric material such as silicone) and the second portion may comprise a rigid material (e.g., rigid plastic). For example, the first portion 500-1 (i.e., the first moulded part or portion) may comprise the top shroud 520, the impeller blades 510, and a first fastening portion 550. The second portion 500-2 (i.e., the second moulded part or portion) may comprise the hub 530, the bottom shroud 525, and a second fastening portion 555. The first impeller portion 500-1 and the second impeller portion 500-2 are fastened together by assembling the first fastening portion 550 to the second fastening portion 555.

In the illustrated example, the first fastening portion 550 includes a hub portion 550-1 and radially extending projections 550-2 spaced about the perimeter of the hub portion 550-1 (e.g., see FIG. 5W). The second fastening portion 555 includes an annular slot 555-1 about the hub 530 adapted to receive the hub portion 550-1 of the first fastening portion 550 when assembled, and the second fastening portion 555 includes radially extending slots 555-2 adapted to receive respective projections 550-2 of the first fastening portion 550 when assembled, e.g., to prevent relative rotation. However, it should be appreciated that the first and second fastening portions 550, 555 may comprise other fastening configurations to fasten, interlock, or otherwise interface the first and second impeller portions.

The two portions 500-1 and 500-2 may be fastened or secured together to produce the impeller 500, such as by snap fit, gluing, welding or any number of other suitable methods. Still further, in some forms, the two portions 500-1 and 500-2 may be arranged such that coupling the assembled impeller 500 onto the motor (e.g., via motor shaft) further strengthens the bonding between the portions of the impeller 500. For example, when the hub 530 of impeller 500 is coupled to the rotor or motor shaft (e.g., by a press fit), the fastening (e.g., snap-fit) between the two portions 500-1 and 500-2 may be assisted and tightened by such hub coupling, e.g., the snap-fit fastening may be tightened by the press-fit coupling of the hub to the rotor.

In another example, as shown in FIGS. 5HH and 5II, the first impeller portion 500-1 (i.e., the first moulded part or portion) may comprise the top shroud 520, the impeller blades 510, the hub 530, and a first fastening portion 550. The second impeller portion 500-2 (i.e., the second moulded part or portion) may comprise the bottom shroud 525 (e.g., substantially planar disc) and a second fastening portion 555. In the illustrated example, the first fastening portion 550 comprises a plurality of protrusions or pips 556-1 extending from the flat lower surface of the impeller blades 510 and/or the hub 530, and the second fastening portion 555 comprises a plurality of holes or slots 556-2 in the bottom shroud 525. The two portions 500-1 and 500-2 may be coupled by aligning and engaging the plurality of protrusions or pips 556-1 into respective holes or slots 556-2 and then fastened or secured together, e.g., by heat stake. The protrusions 556-1 and corresponding holes 556-2 may include circular and/or non-circular shapes, e.g., exemplary figures show combination of circular and non-circular shapes for the protrusions/holes which may be arranged along similar or different portions of the impeller relative to one another (e.g., protrusion/hole along radially inner portion of impeller blade, protrusion/hole along radially outer portion of impeller blade, protrusion/hole along hub). It should be appreciated that FIGS. 5HH and 5II are exemplary and the protrusions/holes may include any suitable combination of shapes, sizes, and arrangements to facilitate fastening and alignment of the two portions 500-1 and 500-2. In an example, an increased number of protrusions/holes may be at least partially determinative of the strength of the joint.

In an example, as shown in FIGS. 5JJ, a relatively sharp end of the blade tip of each impeller blade 510 may be filled in to form a thicker protrusion 556-1 adapted to engage within a corresponding slot or cut-away 556-2 in the edge of the bottom shroud 525. Such arrangement avoids construction of a sharp blade tip to facilitate manufacture, e.g., facilitate molding.

FIGS. 5KK and 5LL show another example of an impeller comprising two impeller portions. In the illustrated example, the first impeller portion 500-1 (i.e., the first moulded part or portion) may comprise the top shroud 520, an upper portion 530-1 of the hub 530, and an upper portion 510-1 of each of the plurality of impeller blades 510. In the illustrated example, the second impeller portion 500-2 (i.e., the second moulded part or portion) may comprise the bottom shroud 525, a lower portion 530-2 of the hub 530, and a lower portion 510-2 of each of the plurality of impeller blades 510. The first impeller portion 500-1 and the second impeller portion 500-2 provide generally planar joining geometry or planar surfaces that are fastened together, e.g., by gluing or welding the upper portion 530-1 of the hub 530 to the lower portion 530-2 of the hub 530, and by gluing or welding the upper portion 510-1 of each of the plurality of impeller blades 510 to a respective one of the lower portion 510-2 of each of the plurality of impeller blades 510.

In such example, the first and second portions 500-1, 500-2 may comprise line-of-draw and may be injection molded with relatively simple, rotating tools. For example, the more complex first portion 500-1 may comprise rotating-while-moving-linearly core to form the flow passage inlets and line-of-draw for the remainder of the flow passage, and the simpler second portion 500-2 may comprise the bottom shroud (e.g., substantially planar disc) with line-of-draw for partial blades.

In an example, as shown in FIGS. 5MM and 5NN, the upper portion 530-1 of the hub 530 of the first portion 500-1 may comprise a cylindrical protrusion 557-1 adapted to engage within the central opening 557-2 provided by the lower portion 530-2 of the hub 530 of the second portion 500-2. Such arrangement provides a concentric alignment detail (i.e., cylindrical locating interfaces between the first and second portions 500-1, 500-2) to the hub to facilitate alignment and concentricity of the first and second impeller portions 500-1, 500-2 when fastened to one another.

In another example, as shown in FIGS. 5OO and 5PP, the lower portion 530-2 of the hub 530 of the second portion 500-2 may comprise a protrusion 558-1 (e.g., generally cylindrical protrusion) adapted to engage within an opening 558-2 provided in the upper portion 530-1 of the hub 530 of the first portion 500-1. Such arrangement provides a concentric alignment to the hub to facilitate alignment of the first and second portions 500-1, 500-2 when fastened to one another.

It will of course be understood that this would not be limited to impellers consisting of two portions, however any number of portions may be assembled together to produce an impeller.

For example, in an alternative example, an impeller may comprise three impeller portions that are fastened or secured together to produce the impeller. For example, as shown in FIG. 5QQ, a first impeller portion 500-1 may comprise the bottom shroud 525 and the hub 530 structured for coupling to the rotor, a second impeller portion 500-2 may comprise the plurality of impeller blades 510 (e.g., 11 impeller blades), and a third impeller portion 500-3 may comprise the top shroud 520. In an example, each of the first, second, and third impeller portions 500-1, 500-2, 500-3 may comprise a molded construction of plastic material. In an exemplary first step, using a fixture, the first and second impeller portions 500-1, 500-2 may be assembled to one another, e.g., the plurality of impeller blades 510 may be secured (e.g., laser or sonic weld) to the bottom shroud 525 and the hub 530. In an exemplary second step, using a second fixture, the third impeller portion 500-3 may be assembled to the assembled first and second impeller portions 500-1, 500-2, e.g., the top shroud 520 may be secured (e.g., laser or sonic weld) to the assembled bottom shroud 525, hub, 530 and impeller blades 510.

In another example, as shown in FIGS. 5RR, 5SS, and 5TT, the impeller may comprise a three-part injection molded construction. For example, the first impeller portion 500-1 (i.e., the first moulded part or portion) may comprise the top shroud 520, an upper portion 530-1 of the hub 530, and an upper portion 510-1 of each of the plurality of impeller blades 510. In the illustrated example, the second impeller portion 500-2 (i.e., the second moulded part or portion) may comprise the bottom shroud 525, a lower portion 530-2 of the hub 530, and a lower portion 510-2 of each of the plurality of impeller blades 510. In the illustrated example, the third impeller portion 500-3 (i.e., the third moulded part or portion) may comprise a cylindrical hub portion 530-3 of the hub 530. In an exemplary first step, the first and second portions 500-1 and 500-2 may be engaged or interlocked by aligning and engaging fastening portions provided to the first and second portions 500-1 and 500-2, e.g., aligning and engaging plurality of protrusions or pips 556-1 provided to the first portion 500-1 into respective holes or slots 556-2 provided to the second portion 500-2, e.g., as described above. In an exemplary second step, the third portion 500-3 may be injection molded to the first and second portions 500-1 and 500-2 to fasten the first and second portions 500-1 and 500-2 to one another, e.g., cylindrical hub portion 530-3 injection molded between the upper and lower portions 530-1, 530-2 to form the hub 530 and fasten the first and second portions 500-1 and 500-2.

5.4.1.1.2 Exemplary Blower

FIG. 5FF shows a blower 600 for an RPT device including impellers 500 according to one aspect of the present technology. In the illustrated example, the blower 600 includes a two-stage design structured and configured for producing a flow, or a supply, of air at positive pressure, e.g., in the range of 4-30 cmH$_2$O. In an example, the RPT device is configured to deliver the flow of air from the outlet for delivery to the patient at a pressure between 4-30 cm$_2$O at an overall sound power level of less than 50 dB(A) thereby reducing any disturbance to a quality of sleep for the patient. However, in alternative examples, the blower may include a single stage design, a three stage design, or four or more stage designs.

As shown, the blower 600 includes a housing 610 including an axial air inlet (blower inlet) 612 and axial air outlet (blower outlet) 614 between which are located two stages with corresponding impellers 500, i.e., a first impeller 500 positioned on one side of the motor 620 and a second impeller 500 positioned on the other side of the motor 620. The motor 620 includes a rotor 625 to which the impellers 500 are coupled. The impellers 500 are configured to be rotated by the rotor 625 to deliver a flow of air from the inlet 612 toward the outlet 614. However, other suitable impeller arrangements are possible. Each impeller 500 may be followed by a set of stator vanes structured and configured to direct the air flow to the next stage or outlet.

In an example, the housing 610 may comprise a plurality of housing portions (e.g., first housing part including inlet 612, second housing part including outlet 614, and intermediate housing parts (e.g., stationary components providing stator vanes to direct air flow) that are connected to one another (e.g., welded) to a form a substantially sealed structure.

Further examples and details of the blower are described in PCT Patent Application Publication No. WO 2013/020167, which is incorporated herein by reference in its entirety.

According to one aspect of the present technology, a portion of the housing 610 adjacent each impeller 500 may include a radius that substantially corresponds to the radius at the leading edge 523 of the impeller inlet wall 521 of the impeller 500. For example, as best shown on FIG. 5GG, a portion of the housing 610 adjacent the perimeter of the blower inlet 612 includes a generally curved surface, e.g., concave surface 615, spaced from and adjacent the generally curved surface, e.g., convex surface 527, provided at the leading edge 523 of the impeller inlet wall 521. In an example, such generally concave surface 615 of the housing 610 includes a radius that substantially corresponds to a radius of the generally convex surface 527 provided at the leading edge 523 of the impeller inlet wall 521.

The substantially corresponding radiusses, the configuration of the curved channel 650 formed between the surfaces 615, 527 of the housing 610 and the impeller 500, and such curved channel 650 terminating at a point where the tangent would point generally downwards (i.e., towards the impeller as approximated by the short arrow A1 in FIG. 5GG) helps re-circulated flow (indicated by the long arrow A2 in FIG. 5GG) smoothly enter the impeller inlet 522. That is, the curved channel 650 formed by corresponding curved surfaces 615, 527 of the housing 610 and the impeller 500 smoothly directs re-circulated flow into the impeller inlet 522.

5.5 Glossary

For the purposes of the present technology disclosure, in certain forms of the present technology, one or more of the following definitions may apply. In other forms of the present technology, alternative definitions may apply.

5.5.1 General

Air: In certain forms of the present technology, air may be taken to mean atmospheric air, and in other forms of the present technology air may be taken to mean some other combination of breathable gases, e.g. atmospheric air enriched with oxygen.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

Patient: A person, whether or not they are suffering from a respiratory condition.

Pressure: Force per unit area. Pressure may be expressed in a range of units, including $cmH_2O$, g-f/cm2 and hectopascal. 1 $cm_2O$ is equal to 1 g-f/cm2 and is approximately 0.98 hectopascal. In this specification, unless otherwise stated, pressure is given in units of cmH2O.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.5.1.1 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure. 'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cm_2O$ pressure.

5.6 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.7 Reference Signs List

| | |
|---|---|
| impeller | 500 |
| first impeller portion | 500-1 |
| second impeller portion | 500-2 |
| third impeller portion | 500-3 |
| impeller blade | 510 |
| upper portion | 510-1 |
| lower portion | 510-2 |
| impeller blade leading edge | 511 |
| impeller blade trailing edge | 512 |
| inner blade portion | 513 |
| opening | 514 |
| first edge | 515 |
| second edge | 517 |
| curved surface | 519 |
| top shroud | 520 |
| top shroud first portion | 520-1 |
| top shroud second portion | 520-2 |
| inlet wall | 521 |
| impeller inlet | 522 |
| leading edge | 523 |
| impeller outlet | 524 |
| bottom shroud | 525 |
| bottom shroud first portion | 525-1 |
| bottom shroud second portion | 525-2 |
| curved surface | 527 |
| hub | 530 |
| upper portion | 530-1 |
| lower portion | 530-2 |
| hub portion | 530-3 |
| flow passage | 540 |
| first fastening portion | 550 |
| hub portion | 550-1 |
| projection | 550-2 |
| second fastening portion | 555 |
| annular slot | 555-1 |
| slot | 555-2 |
| protrusion | 556-1 |
| hole | 556-2 |
| protrusion | 557-1 |
| opening | 557-2 |
| protrusion | 558-1 |
| opening | 558-2 |
| blower | 600 |
| housing | 610 |
| blower inlet | 612 |
| blower outlet | 614 |
| curved surface | 615 |
| motor | 620 |
| rotor | 625 |
| channel | 650 |
| patient | 1000 |
| bed partner | 1100 |
| patient interface | 3000 |
| seal - forming structure | 3100 |
| plenum chamber | 3200 |
| positioning and stabilising structure | 3300 |
| vent | 3400 |
| connection port | 3600 |
| forehead support | 3700 |
| RPT device | 4000 |
| external housing | 4010 |
| upper portion | 4012 |
| lower portion | 4014 |
| panel | 4015 |
| chassis | 4016 |
| handle | 4018 |
| pneumatic block | 4020 |
| inlet air filter | 4112 |
| blower | 4142 |
| air circuit | 4170 |
| electrical component | 4200 |
| PCBA | 4202 |
| electrical power supply | 4210 |
| input device | 4220 |
| humidifier | 5000 |

The invention claimed is:

1. A compact respiratory therapy device suitable for use by a patient during sleep to provide respiratory pressure therapy, the device comprising:
   a housing;
   an inlet;
   an outlet;
   a motor including a rotor;
   an impeller configured to be rotated by the rotor to deliver a flow of air from the inlet toward the outlet, the impeller comprising:
      a first moulded part comprising a plurality of impeller blades, each impeller blade comprising a leading edge and a trailing edge; and a first shroud comprising a wall forming a periphery of an impeller inlet; and
      a second moulded part comprising a hub configured to couple to the rotor and a second shroud,
   wherein the first moulded part comprises a separately moulded and distinct element from the second moulded part, and
   wherein the first moulded part is configured to be coupled to the second moulded part to form the impeller,
   wherein the compact respiratory therapy device is configured to deliver the flow of air from the outlet for delivery to the patient at a pressure between 4-30 cmH$_2$O at an overall sound power level of less than 50 dB (A) thereby reducing any disturbance to a quality of sleep for the patient, and
   wherein:
   a diameter of the impeller is less than about 50 mm, and
   each shroud at least partly forms a flow passage through the impeller.

2. The compact respiratory therapy device as claimed in claim 1, wherein the first moulded part is fastened to the second moulded part by a snap fit to form the impeller.

3. The compact respiratory therapy device as claimed in claim 2, wherein the hub is coupled to the rotor by a press fit, and the snap fit fastening between the first moulded part and the second moulded part is assisted by the press fit coupling of the hub to the rotor.

4. The compact respiratory therapy device as claimed in claim 1, wherein the first moulded part is fastened to the second moulded part by welding to form the impeller.

5. The compact respiratory therapy device as claimed in claim 1, wherein:
   the first moulded part further comprises an outer portion of the second shroud which forms an outer circumference of the first moulded part, and
   the second moulded part further comprises an outer portion of the first shroud which form an outer circumference of the second moulded part.

6. The compact respiratory therapy device as claimed in claim 5, wherein the second moulded part further comprises inner blade portions which add interior rigidity to the impeller blades.

7. The compact respiratory therapy device as claimed in claim 6, wherein the inner blade portions are configured to be received in corresponding openings provided within each of the impeller blades.

8. The compact respiratory therapy device as claimed in claim 5, wherein the first moulded part comprises silicone.

* * * * *